(12) United States Patent
Johnson

(10) Patent No.: US 8,706,528 B2
(45) Date of Patent: Apr. 22, 2014

(54) PRICING AND DISTRIBUTION OF MEDICAL DIAGNOSTICS

(76) Inventor: Alexander Laurence Johnson, San Francisco, CA (US)

( * ) Notice: Subject to any disclaimer, the term of this patent is extended or adjusted under 35 U.S.C. 154(b) by 649 days.

(21) Appl. No.: 12/499,505

(22) Filed: Jul. 8, 2009

(65) Prior Publication Data

US 2010/0010835 A1    Jan. 14, 2010

Related U.S. Application Data

(60) Provisional application No. 61/079,272, filed on Jul. 9, 2008.

(51) Int. Cl.
    *G06Q 10/00*      (2012.01)
    *G06F 19/00*      (2011.01)
    *A61B 5/00*      (2006.01)

(52) U.S. Cl.
    USPC ............................... 705/3; 600/300

(58) Field of Classification Search
    USPC ............................................................ 705/3
    See application file for complete search history.

(56) References Cited

U.S. PATENT DOCUMENTS

| | | | |
|---|---|---|---|
| 6,070,155 A | 5/2000 | Cherrington et al. | |
| 6,149,585 A | 11/2000 | Gray | |
| 6,381,576 B1 * | 4/2002 | Gilbert | 705/2 |
| 6,754,655 B1 * | 6/2004 | Segal | 1/1 |
| 7,523,043 B2 * | 4/2009 | Kantrowitz | 705/2 |
| 2002/0065758 A1 | 5/2002 | Henley | |
| 2003/0069760 A1 | 4/2003 | Gelber | |
| 2004/0143460 A1 | 7/2004 | Marhaver | |
| 2004/0236602 A1 | 11/2004 | Greene | |
| 2005/0228699 A1 | 10/2005 | Samuels et al. | |
| 2005/0278196 A1 | 12/2005 | Potarazu et al. | |
| 2006/0020493 A1 | 1/2006 | Cousineau et al. | |

(Continued)

OTHER PUBLICATIONS

C. Humphreys et al., "Cost-minimization analysis of two algorithms for diagnosing acute pulmonary embolism", Abstract, Thrombosis Research, 2004, [online] [retrieved on Sep. 5, 2008] Retrieved from the Internet at URL:<< http://www.sciencedirect.com/science?_ob=ArticleURL&_udi=B6T1C-4C8P6K1-1&_user=6540578&_coverDate=12%2F31%2F2004&_rdoc=3&_fmt=high&_orig=browse&_srch=doc-info(%23toc%234887%232004%-23998869994%23504018%23FLA%23display%23Volume)&_cdi=4887&_sort=d&_docanchor=&_ct=12&_acct=C000069621&_version=1&_urlVersion=0&_userid=6540578&md5=ba8f668d49fa383dd09d4d f054bb6262>> 3 pages.

(Continued)

*Primary Examiner* — Hiep V Nguyen
(74) *Attorney, Agent, or Firm* — Cooley LLP

(57) ABSTRACT

In one embodiment, a method of pricing a diagnostic test includes receiving data associated with the diagnostic test and setting a price of the diagnostic test. The data associated with the diagnostic test includes an indication of one of a first result of the diagnostic test and a second result of the diagnostic test. The price of the diagnostic test is set based on the indication included in the data associated with the diagnostic test. In another embodiment, a method of pricing a diagnostic test includes receiving data associated with the diagnostic test and charging a first price or a second price for the diagnostic test. The data associated with the diagnostic test includes an indication of one of a first result of the diagnostic test and a second result of the diagnostic test. The first price is charged if the indication is of the first result. The second price is charged if the indication is of the second result. The second price is greater than the first price.

47 Claims, 7 Drawing Sheets

(56) References Cited

U.S. PATENT DOCUMENTS

| | | | |
|---|---|---|---|
| 2006/0155616 | A1 | 7/2006 | Moore et al. |
| 2006/0195342 | A1* | 8/2006 | Khan et al. .................... 705/3 |
| 2007/0088564 | A1 | 4/2007 | March, Jr. et al. |
| 2007/0244720 | A1 | 10/2007 | Walker |
| 2007/0250343 | A1 | 10/2007 | Sohal |
| 2007/0260471 | A1 | 11/2007 | Krassinger et al. |
| 2007/0299690 | A1 | 12/2007 | Frank et al. |
| 2007/0299790 | A1 | 12/2007 | Berkovitz et al. |
| 2008/0010097 | A1 | 1/2008 | Williams et al. |
| 2008/0103895 | A1 | 5/2008 | Burdick et al. |

OTHER PUBLICATIONS

Y. Takemura et al., "Yield and Cost of Individual Common Diagnostic Tests in New Primary Care Outpatients in Japan", [online] [retrieved on May 20, 2008] Retrieved from the Internet at URL:<<http://www.clinchem.org/cgi/content/full/48/1/42>> 16 pages.

KK Jain, "Information on commercial aspects of pharmacogenomics" Pharmacogenomics, 2003, vol. 4, No. 6, pp. 801-803.

J. Jørgensen, "From blockbuster medicine to personalized medicine", Personalized Medicine, 2008, vol. 5, No. 1, pp. 55-63.

K. Phillips et al., "An introduction to cost-effectiveness and cost-benefit analysis of pharmacogenomics" Pharmacogenomics, 2003, vol. 4, No. 3, pp. 231-239.

P. Danzon et al., "The Economics of Gene Therapy and of Pharmacogenetics" Value in Health, 2002, vol. 5, No. 1. pp. 5-13.

T. Dervieux et al., "Overview of the pharmacoeconomics of pharmacogenetics" Pharmacogenomics, 2006, vol. 7, No. 8, pp. 1175-1184.

S. Stallings et al., "A framework to evaluate the economic impact of phannacogenomics", Phannacogenomics, 2006, vol. 7, No. 6, pp. 853-862.

A. Pollack, "Pricing Pills by the Results", [online] [retrieved on Aug. 13, 2008] Retrieved from the Internet at URL:<<http://www.nytimes.com/2007/07/14/business/14drugprice.html>> 4 pages.

* cited by examiner

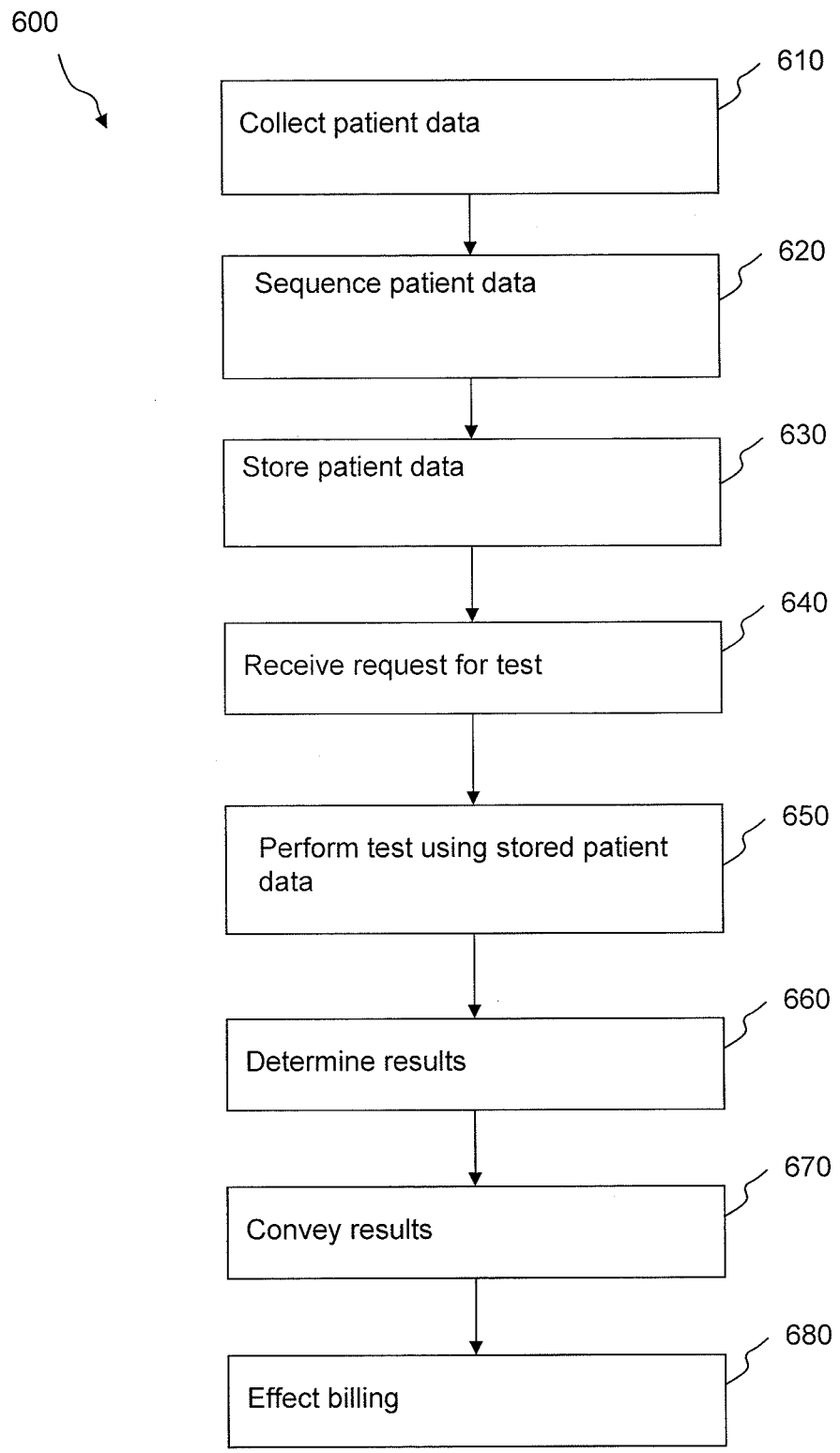

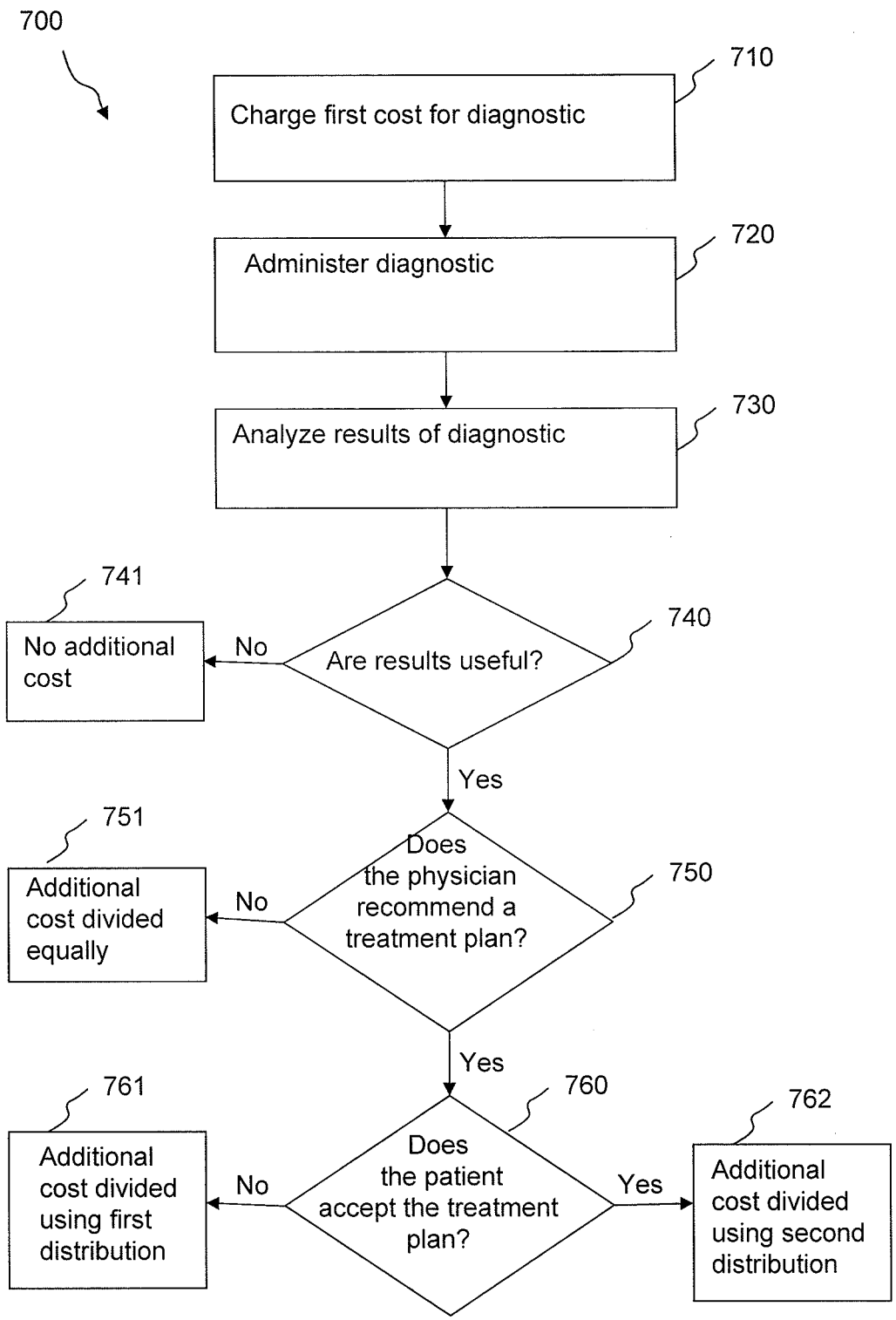

PRICING AND DISTRIBUTION OF MEDICAL DIAGNOSTICS

CROSS-REFERENCE TO RELATED APPLICATION

This application claims priority to U.S. Patent Application Ser. No. 61/079,272, filed on Jul. 9, 2008 and entitled "Pricing and Distribution of Medical Diagnostics," which is incorporated herein by reference in its entirety.

BACKGROUND

The disclosed embodiments relate generally to pricing medical diagnostics including, for example, medical diagnostics for determining whether a patient has or is likely to develop a disease, or the suitability of a therapeutic treatment. Methods and apparatus according to various embodiments are capable of, for example, pricing a medical diagnostic based on value created by the medical diagnostic.

Certain medical diagnostic tests ("diagnostics") such as molecular diagnostic tests can be intended to be predictive of the efficacy, safety and/or response of particular therapeutic regimens. The Food and Drug Administration ("FDA") may, for example, require the availability and use of a diagnostic test prior to administration and use of certain pharmaceutical therapies.

Such a requirement or clinical obligation for use of a companion diagnostic test before starting a drug regime presents a problem for drug manufacturers that do not currently control (e.g., own) and price the diagnostic (or intellectual property related to the diagnostic). The manufacturer of the diagnostic, for example, in order to maximize profit, has an incentive to price the diagnostic very high due to its high economic utility and one-time use. The manufacturers and/or distributors of therapeutic drugs (or other complementary products or therapeutic treatments) have an opposing pricing viewpoint. Such manufacturers and/or distributors would prefer that the diagnostic be priced low, such that more individuals can be tested and, subsequently, begin a therapeutic treatment utilizing the manufacturer's products.

Additionally, the typical usage profile of a diagnostic is a single use and the typical usage profile of a therapeutic treatment is ongoing use. Due to these different usage profiles, the combined economic value of the diagnostic and the therapeutic treatment may be greatest if the diagnostic has a low price. Thus, the high price of some diagnostics and low disease rates of the diseases for which the diagnostics test can make broad screening with diagnostics uneconomical even if the diagnostic is highly accurate.

Methods of pricing diagnostics are known. For example, one such method includes the price of a medical diagnostic in the average price of a comprehensive treatment of a condition indicated by the diagnostic. Thus, an individual who is tested with the medical diagnostic for a medical condition and undergoes a treatment for the medical condition will be charged the same price as other individuals receiving the diagnostic and treatment.

Some known pricing methods allow a user to pay a fixed cost of a medical diagnostic or medical treatment over a period of time. For example, a patient can make monthly payments on the cost of a medical diagnostic or medical treatment for a number of years to spread the cost of the diagnostic and/or treatment over time.

However, known diagnostic pricing methods fail to provide incentives for diagnostic manufacturers to price diagnostics such that the combined medical and/or economic value between a diagnostic manufacture and drug manufactures can be advantageously realized. Furthermore, known diagnostic pricing methods fail to encourage testing or screening of large populations to determine whether certain therapeutic treatments can be beneficial to individuals in these populations. Thus, a need exists for improved pricing methods for diagnostics.

SUMMARY

In one embodiment, a method of pricing a diagnostic test includes receiving data associated with the diagnostic test and setting a price of the diagnostic test. The data associated with the diagnostic test includes an indication of one of a first result of the diagnostic test and a second result of the diagnostic test. The price of the diagnostic test is set based on the indication included in the data associated with the diagnostic test.

In another embodiment, a method of pricing a diagnostic test includes receiving data associated with the diagnostic test and charging a first price or a second price for the diagnostic test. The data associated with the diagnostic test includes an indication of one of a first result of the diagnostic test and a second result of the diagnostic test. The first price is charged if the indication is of the first result. The second price is charged if the indication is of the second result. The second price is greater than the first price.

In another embodiment, a method of determining a price for a diagnostic test includes receiving data associated with the diagnostic test, calculating a value of the diagnostic test, and determining the price for the diagnostic test. The data associated with the diagnostic test includes an indication of one of a first result of the diagnostic test and a second result of the diagnostic test. The value of the diagnostic test is calculated based on the indication included in data associated with the diagnostic test. The price for the diagnostic test is determined based on the value of the diagnostic test.

In another embodiment, a method of pricing a diagnostic test includes charging a first price for the diagnostic test, receiving data associated with the diagnostic test, and charging one of a second price and a third price for the diagnostic test. The first price is charged before administration of the diagnostic test. The data associated with the diagnostic test includes an indication of one of a first result of the diagnostic test and a second result of the diagnostic test. The second price is charged if the indication is of the first result, and the third price is charged if the indication is of the second result.

In another embodiment, a method of distributing a diagnostic test includes, providing a diagnostic test to a first party, receiving data associated with a result of the diagnostic test, collecting from the first party a first cost, and providing a portion of the first cost to a second party. The first party effects administration of the diagnostic test. The first cost is based on the result of the diagnostic test.

BRIEF DESCRIPTION OF THE DRAWINGS

FIG. 6 is a flow chart of a process for performing a diagnostic, according to an embodiment.

FIG. 7 is a flow chart of a process for realizing a multi-part pricing structure, according to an embodiment.

DETAILED DESCRIPTION

Figure 1:
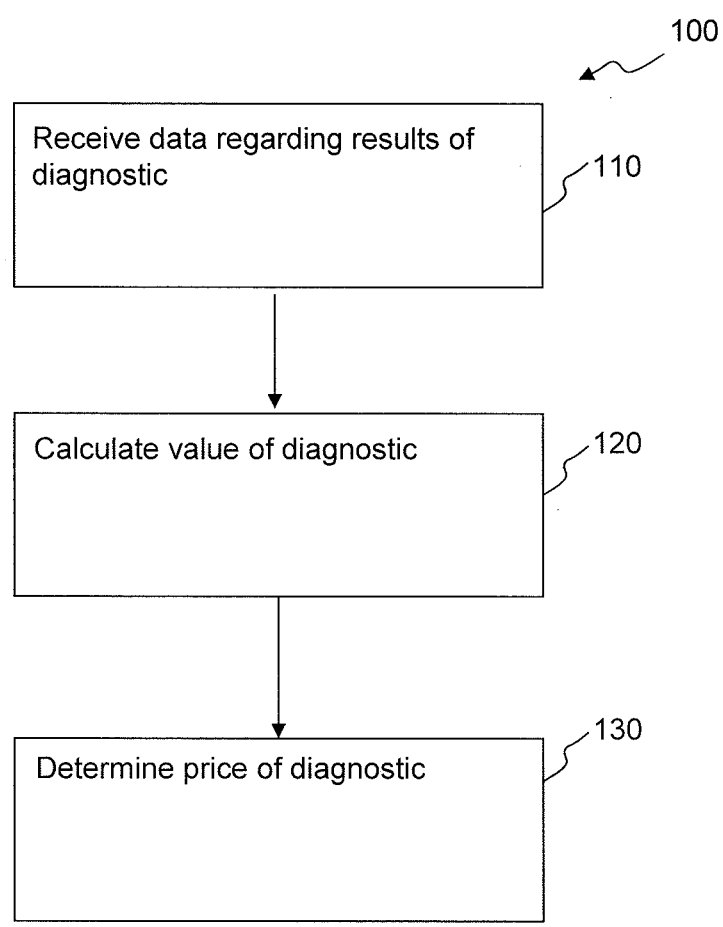
FIG. 1 is a flow chart of a process for determining a price of a diagnostic, according to an embodiment.

Methods and apparatus according to various embodiments can encourage the use of potentially beneficial diagnostic tests within clinical settings. For example, these embodiments separately and/or together create mechanisms and systems for logically and analytically transferring portions of the economic value of diagnostic tests among various parties involved in medical diagnosis and treatment. In doing so, methods and apparatus can transform economically unrelated diagnostics and therapeutics into an integrated optimizing pricing configuration by creating economic incentives for both the development, production, and maximum use of such diagnostics. For example, some of the economic value (e.g., revenue from drug sales) generated when a diagnostic indicates use of a particular drug will likely be beneficial for an individual can be transferred from the manufacturer of drug to the manufacturer of the diagnostic test.

Such value transfer can be particularly useful with diagnostics that screen for diseases that have a very low probability of occurrence, because the value of diagnostics can be significantly less than economic costs of the diagnostic for individuals, insurance companies and/or drug manufacturers. For example, the cost of administering a diagnostic test to screen a large population to determine if a drug will be beneficial to each individual in the population can be prohibitively expensive for a drug manufacturer who does not own the diagnostic (or intellectual property related to the diagnostic). If the cost of the diagnostic test is high and the probability or prevalence of the genetic condition being tested is low, the cost of the diagnostic will often be many times greater than revenue from sales of the therapeutic because the drug will be beneficial for only a small number of individuals in the population. However, if the cost (e.g., cost charged for administration or use) of the diagnostic test is low and the diagnostic manufacturer shares in the revenue generated by drug sales, the drug company can afford to screen larger populations. Additionally, a low-cost diagnostic allows physicians to liberally test or screen patients for treatable conditions, suitability of specific drugs, and other medically useful information.

Diagnostic tests as used herein include tests for determining the suitability of one or more therapeutic treatments for an individual and include, for example, molecular diagnostic tests, genetic tests, and other medical tests. A therapeutic treatment can be any method of treating a medical or physiological condition. For example, a therapeutic treatment can be use of a drug or other therapeutic compound, a change in lifestyle or diet, physical therapy, and/or gene therapy. Diagnostic tests can be used, for example, to determine whether a person has or is likely to have a disease or disorder; determine whether a person will or likely will positively react to a particular therapeutic treatment; determine whether a person will or likely will have an adverse reaction to a particular therapeutic treatment; and/or determine whether a person will or likely will develop a disease or disorder. Thus, information gained or derived from such diagnostics can help to create economic and other benefits resulting from individual, or population-specific guidance to, for example, chose a therapy over no therapy, chose one course of therapy over alternatives, choose a combination of therapies over alternatives, avoid a particular course of therapy, and/or create lifestyle changes based on results of diagnostics.

In one embodiment, the manufacturer of a diagnostic test provides the diagnostic test to the manufacturer of a drug that treats a medical condition screened for by the diagnostic test at a low price. For example, the diagnostic test can be provided free of charge or for a nominal charge. The drug manufacturer can use the diagnostic to screen a large number of individuals to determine whether a drug will be beneficial for particular individuals. Because the diagnostic test is provided for a low price, the drug manufacturer can screen many individuals without incurring unmanageable costs. The diagnostic allows the drug manufacturer to access a broader market of potential customers for the drug by demonstrating to the potential customers that the drug will be beneficial to them, based on results of the diagnostic test. The drug manufacturer is able recoup the costs of the diagnostic tests through revenue generated by drug sales to individuals who buy the drug based on the diagnostic test.

After the drug manufacturer has used the diagnostic to determine whether a drug will be beneficial to an individual and the individual purchases the drug, the drug manufacturer makes additional payments to the manufacturer of the diagnostic. This allows the diagnostic manufacturer to collect or share in downstream profitability and revenues that result from use of the diagnostic. For example, if a result of a diagnostic test indicates that an individual will benefit from taking a drug for a period of time, the drug manufacturer can make recurring payments to the manufacturer of the diagnostic test for the period of time the individual is taking or using the drug. These payments can be based on, for example, the value generated by the diagnostic test (e.g., the revenue the drug manufacturer will receive from an individual to whom the diagnostic test was administered).

For example, consider a class of drugs for lipid-lowering therapy in the prevention of coronary heart disease known as statins. These life saving drugs would appear to be a natural fit for pharmacogenomic diagnostic testing. Yet today, statin response testing is uncommon. An impediment to statin response testing lies with the multitude of prescription choices for physicians and patients. For example, statin choices include: Fluvastatin, Lovastatin, Mevastatin, Pitavastatin, Pravastatin, Rosuvastatin, Simvastatin, Simvastatin+Ezetimibe, Lovastatin+Niacin, and Atorvastatin+Amlodipine Besylate. Thus, even if diagnostic tests for a particular group of statin drugs or therapies are readily available, it is not clear which tests a physician should administer. The costs to test all drugs or therapies would be prohibitive, and moreover such a test cost would be wasted if the patient switched to a new therapy a short time later. Instead, the physician will often prescribe a certain statin, and if it does not give the intended effect, will switch the patient to the next choice. A more efficient method, described herein, includes transforming these individual tests, drugs, and/or therapies into a consolidated pricing model whereby the patient is tested for a low or nominal cost for all tests. The therapeutic manufacturer that benefits from the tests, drugs, and/or therapies (e.g., the therapeutic manufacturer that sells a drug based on the positive diagnostic test) then effectively pays for the test price because that test generated benefit to that particular therapeutic manufacturer.

As used in this specification, the singular forms "a," "an" and "the" include plural referents unless the context clearly dictates otherwise. Thus, for example, the term "a diagnostic" is intended to mean a single diagnostic or a combination of diagnostics, "a manufacturer" is intended to mean one or more manufacturers, or a combination thereof.

FIG. 1 is a flow chart of process 100 for determining a price of a diagnostic, according to an embodiment. Data regarding the results of a diagnostic are received at 110. The data can be any representation or indication of the results of a diagnostic and/or including the results of a diagnostic. The data can be, for example, a report including the results of the diagnostic, or data from the diagnostic that has not been previously analyzed to determine a result of the diagnostic. In some embodiments, the data are digital data such as, for example, a digital representation of a mass spectrum or assay analysis of a diagnostic. In some embodiments, the data are a biological sample such as, for example, a blood sample and/or a tissue sample. In some embodiments, the data can be a report such as, for example, an electronic or paper document including information associated with the diagnostic.

The result of the diagnostic can indicate, for example, that a person has or is likely to have a disease or disorder; that a person will or likely will positively react to a particular therapeutic treatment; that a person will or likely will have an adverse reaction to a particular therapeutic treatment; and/or that a person will or likely will develop a disease or disorder. In some embodiments, the result of the diagnostic indicates a first biological state or a second biological state such as, for example, the presence of a disease or the absence of a disease. In some embodiments, for example, a diagnostic can determine the presence of cancer in an individual (a first biological state) or the absence of caner in the individual (a second biological state).

In some embodiments, the result of a diagnostic indicates the likelihood of one or more conditions, or an outcome of one or more conditions. For example, a diagnostic can indicate that an individual will likely respond positively to a therapeutic treatment such as, for example, a treatment period or regime with a particular drug or a gene therapy treatment. In some embodiments, a diagnostic can indicate that an individual is likely to develop a disease or disorder. In other embodiments, a diagnostic can indicate that an individual will or likely will have an adverse reaction to a therapeutic treatment.

A value of the diagnostic is determined at 120 of process 100. The value of a diagnostic can be, for example, an economic benefit, a non-economic benefit and/or a combination of economic and non-economic benefits to one or more individuals or entities as described in more detail below. Non-economic benefits include, for example, quality of life, improved mobility, and/or the ability to enter or re-enter the workforce. For example, health attributable to discovery by a screening diagnostic of a disease in early or treatable stages that is subsequently successfully treated, is a value or benefit to the individual successfully treated for the disease.

A value of a diagnostic can be calculated using various methodologies. Any methodology of assigning a value to benefits enabled by a diagnostic may be used. As described as an example in more detail below, a value can be calculated based on the value of a particular result to one or more interested parties. Also, as described as an example in more detail below, a value can be determined based on economic modeling or economic value analysis.

In some embodiments, the value is calculated or determined based on a result of a diagnostic. For example, a result indicating the presence of a disease in an early or treatable stage can have value and be beneficial to an individual and an insurance company because the disease can be treated with less cost and better results than if the disease was discovered in an advanced stage of the disease. Such a result can also be beneficial to drug manufacturer if its drug is used in treating the disease. A result indicating the absence of a disease, or that a particular therapeutic treatment will be ineffective, can also have value to an individual and an insurance company.

Such a result can, for example, prevent unnecessary expenditure on unnecessary therapeutic treatments. In some embodiments, the value is determined based on multiple results of one or more diagnostics. In other embodiments, the value is predetermined based on expected results of a diagnostic.

In some embodiments, diagnostic value can be ascertained through economic value analysis such as, for example cost of illness analysis, cost minimization analysis, cost benefit analysis, cost effectiveness analysis and/or cost utility analysis. For example, a typical cost-benefit analysis as described in Dervieux & Bala, "Overview of Pharmacoeconomics of Pharmacogenetics", Pharmacogenomics (2006); 7(8):1175-1204, which is incorporated herein by reference in its entirety, includes Quality-Adjusted Life Years ("QALY") calculations dependent on clinical performance of a genetic test. In such calculations, the value of the diagnostic may be ascertained by comparing two or more healthcare procedures. Cost is calculated in monetary units and benefits are expressed in physical units, such as side affect avoided, or incremental years of life saved. The value of the test may be expressed in terms of QALY, and compared to alternatives, creating a basis for measuring incremental value.

In some embodiments, the value of a diagnostic is the revenue to the manufacturer of a therapeutic treatment or other party generated by results of a diagnostic that lead directly or indirectly to the use of a specific therapeutic compound and/or treatment, device, regimen, or additional diagnostic. The manufacturer of a therapeutic treatment or other party receiving this value, transfers some of the value to the diagnostic manufacture. For example, a drug manufacturer or drug manufacturers make payments to the manufacturer of a diagnostic whenever an individual begins a regimen of prescription drugs based on the results of the diagnostic. Thus, if a test leads to therapy, the payment scheme is triggered by the use of the therapy that the diagnostic has recommended and/or predicted will or likely will be successful, and the diagnostic manufacturer is able to profit from the value generated or realized. In some embodiments, the value is a recurring value such as, for example, monthly sales of a prescription drug to an individual by a drug manufacturer.

For example, consider another statin example. If the statin diagnostic manufacturer is able to create a useful action (in the form of the patient staying on a particular statin for many years), the diagnostic manufacturer would receive periodic payments from that statin manufacturer, for as long as the patient stayed on that statin. For a statin manufacturer with a therapy with a small available percentage of the market (as defined by low response rate among individuals), this system transforms their standalone product into an integrated pay-as-you-go diagnostic-therapeutic model that enables a much higher market penetration than would be affordable if the statin manufacturer tested all patients up front for just their test.

In some embodiments, the value generated by a diagnostic is a savings. For example, savings to an insurance company attributed to beginning treatment of a disease during an early stage of the disease in an individual insured by the insurance company and diagnosed with the disease based on a result of a diagnostic. Additionally, a diagnostic can indicate that a drug will be ineffective for a particular patient and, thus, prevent unnecessary expenditures on that drug for the particular patient.

After an estimated value is calculated, the diagnostic pricing is determined for the diagnostic that generated or realized that value at 130. The value can be divided or converted into a price or cost under any number of formulas and including various factors as discussed in more detail below. In some embodiments, the price varies based on the result of the diagnostic. For example, a diagnostic that results in early treatment of a disease or medical disorder and prevents costly complications, for which an insurance company would otherwise make payments, can be priced at a percentage of the savings to the insurance company.

In some embodiments, the price of the diagnostic is paid by the individual to whom the diagnostic is administered. For example, the price can be charged to the patient or individual receiving the diagnostic. In other embodiments, another party receiving value from the diagnostic pays the price of the diagnostic. For example, an insurance company, a healthcare company, a drug manufacturer, and/or a drug distributor can each receive value from the diagnostic and each might pay a portion of the price of the diagnostic.

In some embodiments, the price is extended over a treatment period. For example, a drug manufacturer can make payments to the manufacturer of a diagnostic that produced results causing an individual or insurance company to purchase the drug from the drug manufacturer, each time the individual or insurance company purchases the drug.

In some embodiments, payments are made over the same time period that generally corresponds to the time frame during which value is generated. For example, payments can be made during the course of a therapeutic treatment resulting in payments to the manufacturer of the therapeutic treatment, or during a period of increased health attributable to detection of a medical disorder in an individual by the diagnostic and subsequent therapeutic treatment. The time frame may be set by the parties involved based on clinical and other experience, as well as other relevant or related factors.

In some embodiments, a predetermined fixed price or payment of the diagnostic is initiated by a result of the diagnostic and remitted in stages that approximate the time the diagnostic is expected to provide economic benefit or value. The calculation could be as simple as the diagnostic price divided by the number of years that the diagnostic will provide benefit. For example, a $3,000 diagnostic expected to generate 10 years of sales of a companion drug, might be charged to the drug company in increments of $300 per year for 10 years. This simplistic formula could also be modified to take into account, for example, probability assessments, net present value assumptions, as well as other modifiers that would create a non-linear payment schedule. In some embodiments, the stages or phases of such a schedule are predetermined.

In some embodiments, the price and/or payment schedule of a diagnostic is based on a payment schedule and/or recurring fee or cost of a therapeutic treatment. For example, the price of a diagnostic can be a recurring fee based on a monthly charge for a therapeutic treatment such as a prescription drug dose, a physical therapy regimen, and/or an exercise or preventative care regimen. In some embodiments, price is based on past use of a diagnostic and actual use of a drug that requires, for example, as per an applicable FDA regulation, use of a diagnostic before the drug can be prescribed by a physician.

In some embodiments, the price is modulated (or adjusted) to dynamically reimburse and/or pay diagnostics manufacturers for the resultant downstream profitability of a therapeutic treatment that is enabled by the diagnostic. For example, a prescription drug manufacturer's profitability increases over time as production, distribution, and/or other costs associated with a prescription drug decrease. As the prescription drug manufacturer's profitability increases, the recurring price or cost of the diagnostic increases such that the diagnostic manufacturer is dynamically reimbursed for the profitability or value enabled by the diagnostic. In some embodiments, the recurring price or cost of the diagnostic decreases in response to a decrease in the prescription drug manufacturer's profitability decreases. For example, the prescription drug manufacturer's profitability can decrease after entry into the market of generic variants of a drug. In other words, the value enabled by the diagnostic can be dynamically transferred or shared between a diagnostic manufacturer and a manufacturer of a therapeutic treatment. Such post hoc pricing for the diagnostic enables diagnostic manufacturers and therapeutic treatment manufacturers to maximize the combined amount of profit between them by forgoing value distribution until such value is can be more precisely calculated.

Similarly, in some embodiments, the price is modulated to dynamically reimburse and/or pay diagnostics manufacturers for the resultant downstream profitability of a therapeutic treatment that is solely and/or specifically enabled by the diagnostic. In some embodiments, for example, the diagnostic manufacturer is paid based on the actual prescriptions written, average profitability of new patients, or any other method agreed upon.

In some embodiments, the diagnostic price is set or determined based on an algorithm that divides economic value of a diagnostic between parties associated with the results of the diagnostic including, for example, parties responsible for selecting a therapy, selecting optimal therapy and/or selecting a change in behavior, lifestyle, or diet. For example, one price can be associated with a physician using the results of a diagnostic to make a medical or health-related recommendation, and another price can be associated with the use of a drug based on the results of the diagnostic.

Process 100 can be rearranged and/or include more or fewer steps. For example, a value of the diagnostic can be predetermined before the diagnostic is administered. In one embodiment, process 100 can include determining whether a result of a diagnostic is one of two or more predetermined results.

Furthermore, in some embodiments, an initial amount is paid at the time the diagnostic is administered, then additional periodic, for example, monthly, quarterly and/or annually, and/or an additional ending reconciling payments are made. Such reconciling payments can be calculated to consider actual payments made or accrued, improved approximations, actual economic value created and/or savings created. Such payments may be netted against the financial impact of other administrations of diagnostics between the same parties and/or other parties to simplify accounting of this pricing embodiment. For example, an insurance company can make a single monthly payment to a diagnostic manufacturer that is based on initial estimates of cost savings and then in a future period paying reconciling amounts based on net calculated savings generated by the administration of such diagnostics to the group, rather than effect payment for each individual diagnostic user.

Additionally, in some embodiments, the payments made, or accrued as a result of the economic value of administration of diagnostic, are refunded if the diagnostic is found to be inaccurate. In other words, if a diagnostic predicts responsiveness to a treatment, or prediction of a disease state, or non-disease state, and such prediction is proven or shown over time to be invalid or incorrect, for example, due to the nature of human disease or treatment effects, then the diagnostic owner, will rebate the price of the diagnostic, or price paid over time.

In some embodiments, an additional refund payment, above and beyond the original, estimated and/or over-time price of the diagnostic is made if the diagnostic is incorrect or inaccurate. In some such embodiments, the diagnostic manufacturer creates the equivalent of an insurance fund pool to pay patients and/or payors of the diagnostic of those patients (e.g., insurance companies and/or healthcare organizations) for whom the diagnostic has generated false positives, false negatives, and/or other incorrect or inaccurate diagnosis or combination of diagnoses.

Consider, for example, a particular diagnostic that is reputed to correctly predict occurrence and/or recurrence of a certain type of a disease 98% of the time. Those 2% of patients who in later years are afflicted with the disease state contrary to the prediction or diagnosis of the diagnostic, will be entitled to a refund of the initial price paid for the diagnostic. In some embodiments, such patients will receive additional payments of a material or non-material amount to, for example, help pay for additional treatment due to an inaccurately predicted disease state. Such payments may be contractually limited to the form of a therapeutic treatment that is linked to the diagnostic, rather than monetary payment.

Such embodiments enable a payment system to function as a warrantee to, for example, create or increase a sense of emotional and financial security to those taking the test. Such a sense of emotional and/or financial security can increase the appeal and use of diagnostics. Thus increasing revenue for diagnostic manufacturers, manufacturers of therapeutic treatments, and/or other parties as greater numbers of individuals are matched with appropriate therapeutic treatments based on results of diagnostics.

Figure 2:
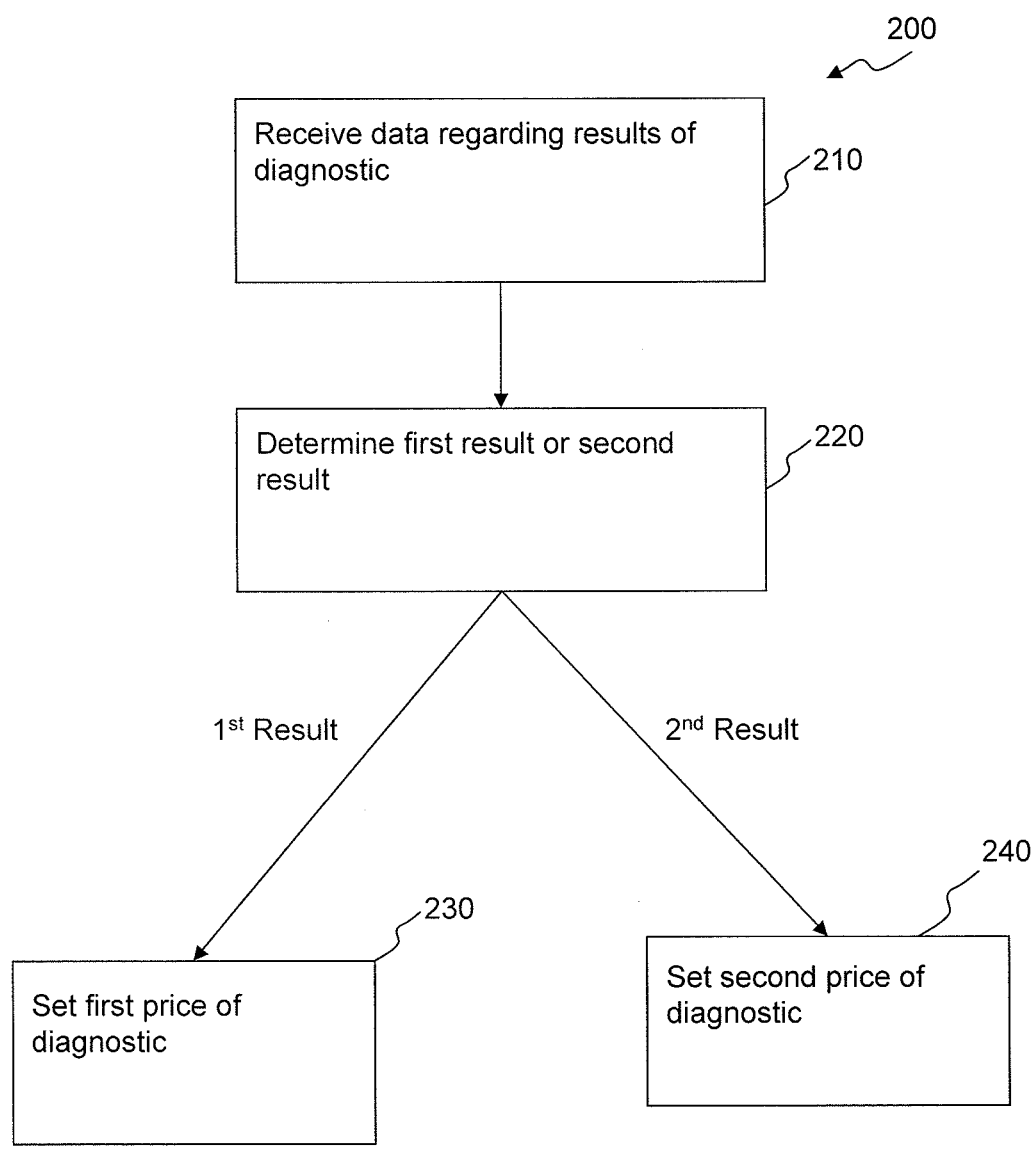
FIG. 2 is a flow chart of a process for determining a price of a diagnostic, according to another embodiment.

FIG. 2 is a flow chart of 200 process for determining a price of a diagnostic, according to another embodiment. Data regarding the results of a diagnostic are received at 210. The data can be any representation or indication of an outcome of a diagnostic and/or can include the results of a diagnostic. The data can be, for example, a report including the results of the diagnostic, data from the diagnostic that have not been previously analyzed to determine a result of the diagnostic, and/or digital data as described above.

As illustrated at 220 of process 200, in some embodiments, it is determined whether the result of a diagnostic is one of two or more results. For example, it can be determined whether the result of the diagnostic indicates a first biological state or a second biological state such as, for example, the presence of a disease (a first biological state) or the absence of a disease (second biological state).

In some embodiments, the result of a diagnostic indicates the likelihood of one or more biological conditions or outcomes of a therapeutic treatment. For example, a diagnostic can indicated that an individual will likely respond positively to a therapeutic treatment such as, for example, a treatment period with a particular drug or a gene therapy treatment. In some embodiments, one result of a diagnostic can indicate that an individual is likely to develop a disease or disorder, and another result can indicate that the individual is not likely to develop the disease or disorder. In other embodiments, a diagnostic can indicate that an individual will or likely will have an adverse reaction to a therapeutic treatment, and another result can indicate that the individual is no likely to have an adverse reaction to the therapeutic treatment.

After the result of the diagnostic is determined, a price or cost to be charged to the payor of the diagnostic is set or determined. As illustrated at 260 and 240 of process 200, the price varies based on the result of the diagnostic and can be determined by various methods, as discussed below. If the result is a first result, a first price is set for the diagnostic, at 260. If the result is a second result, a second price different from the first price is set for the diagnostic, at 240. In some embodiments, a price for a result causing, suggesting, resulting in, or prompting a change in a treatment, a change in lifestyle and/or initiation of a treatment is greater than a result not causing, suggesting, resulting in, or prompting such a change.

In one embodiment, the price of the diagnostic dynamically changes to account for change in economic value with the expected value of the information that may be received, as well as the value of the information that is actually received. For example, if the result is the first result, the price is a nominal administration fee; but if the result is the second result, the price is set as follows:

$$\text{Price Multiplier } A \times \text{Price Multiplier } B \times \text{Base Price of Diagnostic} = \text{Final Price of Test,}$$

where
  Price Multiplier A is related to expected clinical utility of information that relates to the person being tested, including age, disease state, or other independent variable,
  Price Multiplier B is related to the quality of information, where a zero may be recorded for a negative (e.g., non-diseased state) result, to a higher factor for the result of the diagnostic that shows a positive (e.g., diseased state) result and good sensitivity and selectivity data, to a 1.00 for positive data that is virtually unchallengeably useful.

In another embodiment, the price paid or charged for the diagnostic ranges from zero to a full maximum of a list price of the diagnostic. Such a price could be determined using a multiplicative factor could ranging from zero for those testing negative, to, for example, 0.01, 0.02, 0.05, 0.10, 0.15, 0.20, 0.35, 0.40, 0.50, up to 1.00, and possibly exceeding 1.00 depending on the validity, specificity, sensitivity, predictive value, expected clinical utility, outcome or time frame in which the results will show clinical utility, economic benefits and/or other benefits for those testing positive.

For example, a $5,000 base price for a particular result is set for a diagnostic predictive screening test for a cancer typically seen only in women older than 65 years old. If the person tested is an 20-year old woman, the test may be priced using a price factor of 0.20 resulting in an effective price of $1,000 (0.2×$5,000), as might be appropriate for the tested person for whom the diagnostic is expected to have low clinical utility. Such expected utility would be calculated as higher, based on an increased multiplicative factor, for a woman who is aged 40, and still higher for a women aged 60, with corresponding higher prices for the diagnostic due to the higher increased expected utility.

In one embodiment, the payor (e.g., the patient of another entity for which the diagnostic can generate value) is only charged a nominal paperwork fee, for example $20 for each test administered. When a test reveals a positive result (i.e., one with economic or other value), a price of, for example, $3,000 is charged for the diagnostic. If the test reveals a negative result (i.e., one with little or no value), no additional price is charged. In some embodiments, different parties pay for the diagnostic based on the outcome of the diagnostic. For example, the individual receiving the diagnostic pays for the diagnostic if the result is negative, and an insurance company pays for the diagnostic if the result is positive.

In some embodiments, the price is charged to and/or paid by a party other than an individual receiving a diagnostic. For example, a drug company administering the diagnostic to screen for individuals to whom its drug will be beneficial may pay the price to a diagnostic manufacturer or distributor. In some embodiments, the price of the diagnostic may be charged to the insurance company insuring an individual receiving the diagnostic.

In some embodiments, process 200 can include additional and/or rearranged steps. For example, process 200 can include one or more steps for determining a value (e.g., economic or societal) of the first result and/or the second result, and the price can be based on the value.

Figure 3:
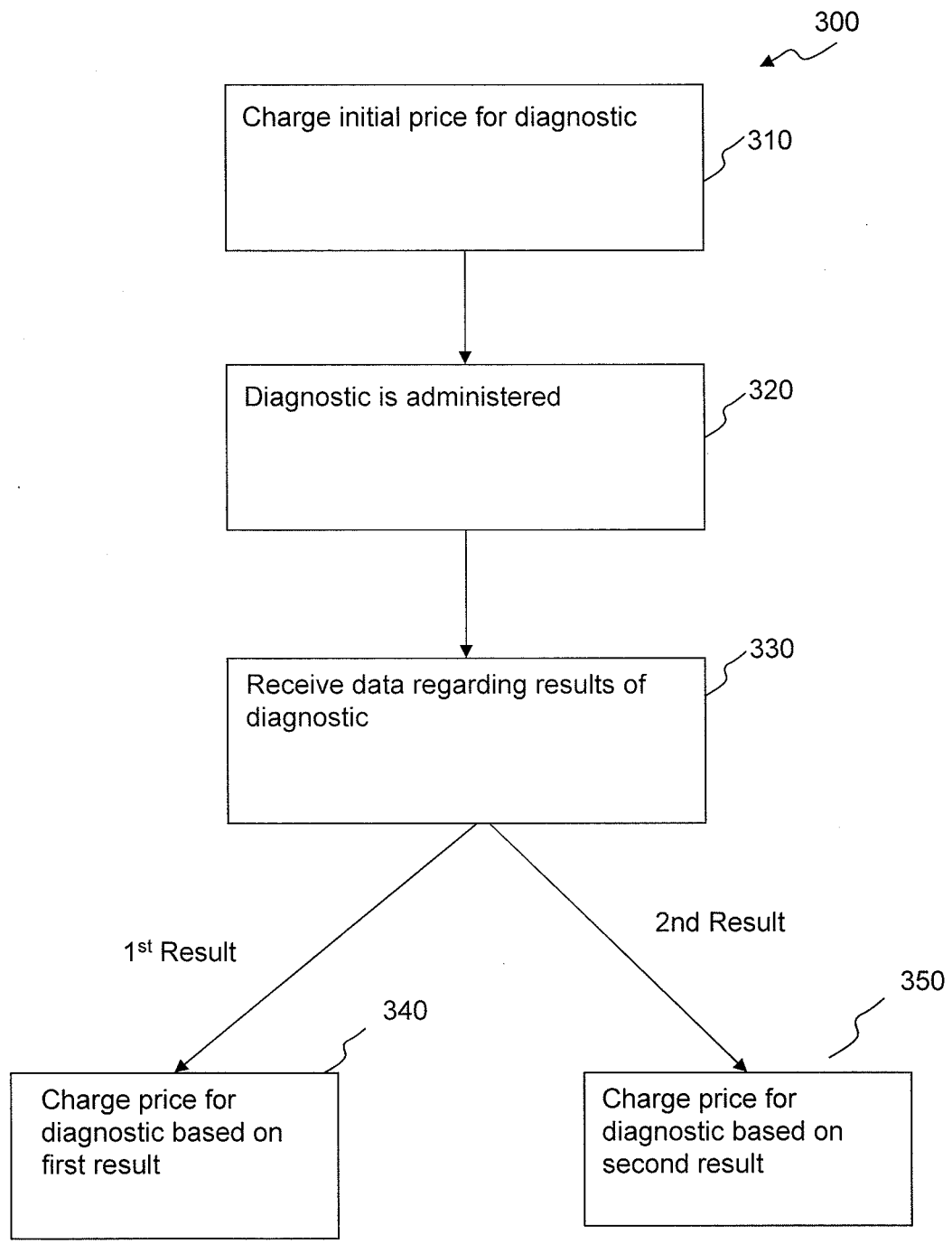
FIG. 3 is a flow chart of a process for determining a price of a diagnostic, according to another embodiment.

FIG. 3 is a flow chart of process 300 for determining a price of a diagnostic, according to another embodiment. An initial price for a diagnostic is charged at 310. The initial price can be, for example, a nominal, minimal or administrative fee or charge. For example, a diagnostic manufacturer can provide a diagnostic to an insurance company for the price of shipping the diagnostic to the insurance company. In some embodiments, the diagnostic can be provided directly to an individual who will use the diagnostic. In some such embodiments, the diagnostic is intended for use without the supervision of a physician. In other embodiments, the initial price can be a more substantial amount, but less than an expected, estimated and/or potential value of the diagnostic or results of the diagnostic.

The diagnostic is administered at 320. The diagnostic can be administered by, for example, a physician to a patient. In some embodiments, administration of the diagnostic can be effected by an insurance company. For example, the insurance company can provide clinics for administering the diagnostic. In some embodiments, an insurance company can indirectly effect administration of the diagnostic. For example, the insurance company can send a diagnostic intended for use without supervision of a physician to an individual. The individual uses the diagnostic and can send the results and/or sample from the diagnostic to the insurance company or some other entity for analysis. In some embodiments, a diagnostic manufacturer can directly or indirectly effect administration of a diagnostic.

Data regarding the results of a diagnostic are received at 330. The data can be any representation or indication of the results of a diagnostic and/or including the results of a diagnostic. The data can be, for example, a report including the results of the diagnostic, data from the diagnostic that have not been previously analyzed to determine a result of the diagnostic, and/or digital data as described above.

As illustrated at 340 and 350 of process 300, the price of the diagnostic varies based on the result of the diagnostic. If the result is a first result, at 340 a first price other than the initial price is charged for the diagnostic. If the result is a second result, at 350 a second price other than the initial price and different from the first price is charged for the diagnostic. The first result can be, for example, a result indicating a diseased state and/or that a particular therapeutic treatment will be effective. The second result can be, for example, a result indicating a non-diseased state and/or that a particular drug will have adverse reactions or be ineffective.

Consider a patient considering whether to pay for a $3,000 test that indicates whether they have a gene variant that enables them to forgo a therapy (such as Interferon for Hepatitis C) that often has debilitating adverse affects. Assume that the gene variant only exists in 10% of the population. Most, if not all patients would find the test useful, since it gives them a chance for a better quality of life. For purposes of this example, assume the value of the incremental quality of life is worth $120,000 per person who does not have to take the therapy. Although the expected value is positive, the chances are so small (1 out of 10) that many will not take the test, just as many rational people have typical psychological biases that prevent them from betting $3,000 to win $120,000 even if the expected value of the bet were in their favor. In the method proposed, the patient has a novel advantage. He or she need not take an expected value "bet". Instead the patient pays if—and only if—the test results benefit him or her. In the proposed method, all patients could take the diagnostic by paying a small fee—perhaps $20.00 to process the sample and deliver results. The testing center would run the patient's test alongside with hundreds, perhaps thousands of identical tests from other patients making for very strong efficiencies. At the conclusion, a second price—say $30,000—is charged if the test delivers useful, valuable results that enable the patient to capture the benefits (worth $120,000) from not taking the debilitating therapy. This method transforms a purchase with probabilistic uncertainty of value into a known and valuable proposition for the customer. The system by which this is effected involves initial tracking and processing of patient results to deliver a billing receipt.

In some embodiments, the first price is greater than the second price because the first result will or will likely generate economic value. For example, an indication that a drug will be effective may generate drug sales for a drug manufacturer. In some embodiments, the second price is higher than the first price because the second result prevents expenditures. For example, an indication that a drug will be ineffective (e.g., because a patient's body will not positively respond to the drug, is not affected by a disease or condition, or will not be affected by a disease or condition) may prevent unnecessary expenditures by an insurance company or an individual.

In some embodiments, the first price is between two and ten times greater than the second price. In some embodiments, the first price is between ten and one hundred times greater than the second price. In some embodiments, the first price is more than one hundred times greater than the second price.

In some embodiments, the price (e.g., an initial price, a first price and/or a second price) of the diagnostic is charged to an individual patient by the diagnostic manufacturer. In another embodiment, the price charged to a manufacturer of a related therapeutic treatment. In another embodiment, the price is charged to a health maintenance organization ("HMO"), preferred/participating provider organization ("PPO"), or similar insurance or managed care provider with economic and contractual recourse for the health costs of the end-user patient.

In some embodiments, various prices associated with a diagnostic are paid by different parties. For example, an initial price for a diagnostic test can be paid by an individual receiving the diagnostic and a first price or a second price based on the result of the diagnostic is paid by an insurance company. In some embodiments, the initial price for a diagnostic can be paid by a drug manufacturer and a first price or a second price based on the result of the diagnostic is paid by an insurance company.

In some embodiments, the charge in addition to the initial price only occurs when the diagnostic provides useful results, which do not necessarily have to be quantitative or qualitative. Usefulness may also be assessed in other methods. Takemura, et al, "Yield and Cost of Individual Common Diagnostic Tests in New Primary Care Outpatients in Japan", Clinical Chemistry, 2002; 48: 42-54, which is incorporated herein by reference in its entirety, is an example of a rating system for assessing usefulness of a diagnostic and describes the ratings system of the Japan Society of Clinical Pathology. Takemura describes a useful result of a diagnostic as a finding that contributed to a change in the physician's diagnosis or decision-making relating to a tentative initial diagnosis ("TID")

based on history and physical examination alone. In addition, a useful result occurs when results of a diagnostic contribute to evaluation of the nature and/or severity of a disease, and are followed by a change in a physician's decision making. For example, a useful result might result in a change in the treatment and/or management of the patient, additional ordering of organ- or disease-specific tests, reference to a specialist, or transfer of a patient to a specific clinic.

In some embodiments, the charge in addition to the initial price for the diagnostic only occurs when the outcome of the diagnostic directly results in prescription of a therapeutic treatment to the patient tested. For example, when the outcome of the diagnostic indicates a diseased state and/or that a particular therapeutic treatment will be effective. In some embodiments, the selection of therapeutic treatment results directly from the information conveyed by the results of the diagnostic.

In some embodiments, the charge in addition to the initial price for the diagnostic only occurs when the outcome of the diagnostic directly results in prescription to the patient tested of a course of therapy that does not include a specific therapeutic treatment or combination of therapeutic treatments. For example, when the outcome of the diagnostic indicates a non-diseased state, that a particular therapeutic treatment will not be effective, and/or that the patient will have adverse reactions to a particular therapeutic treatment. Such outcomes can, for example, prevent unnecessary and/or useless expenditure on therapeutic treatments that would be ineffective. In some embodiments, the selection of the prescribed course of therapy is a result of the information conveyed by the results of the diagnostic.

In some embodiments, process 300 can include additional steps and/or be rearranged. For example, process 300 can include one or more steps for determining whether a therapeutic treatment suggested or recommended based on a result of a diagnostic is useful or beneficial. A therapeutic treatment is useful or beneficial when it effectively treats a medical condition. For example, in some embodiments, no price is charged until a medical condition has been successfully treated with a drug recommended by a diagnostic. Thus, in some embodiments, the price will be charged only when the result, prediction and/or recommendation of a diagnostic is shown to be correct or accurate.

Figure 4:
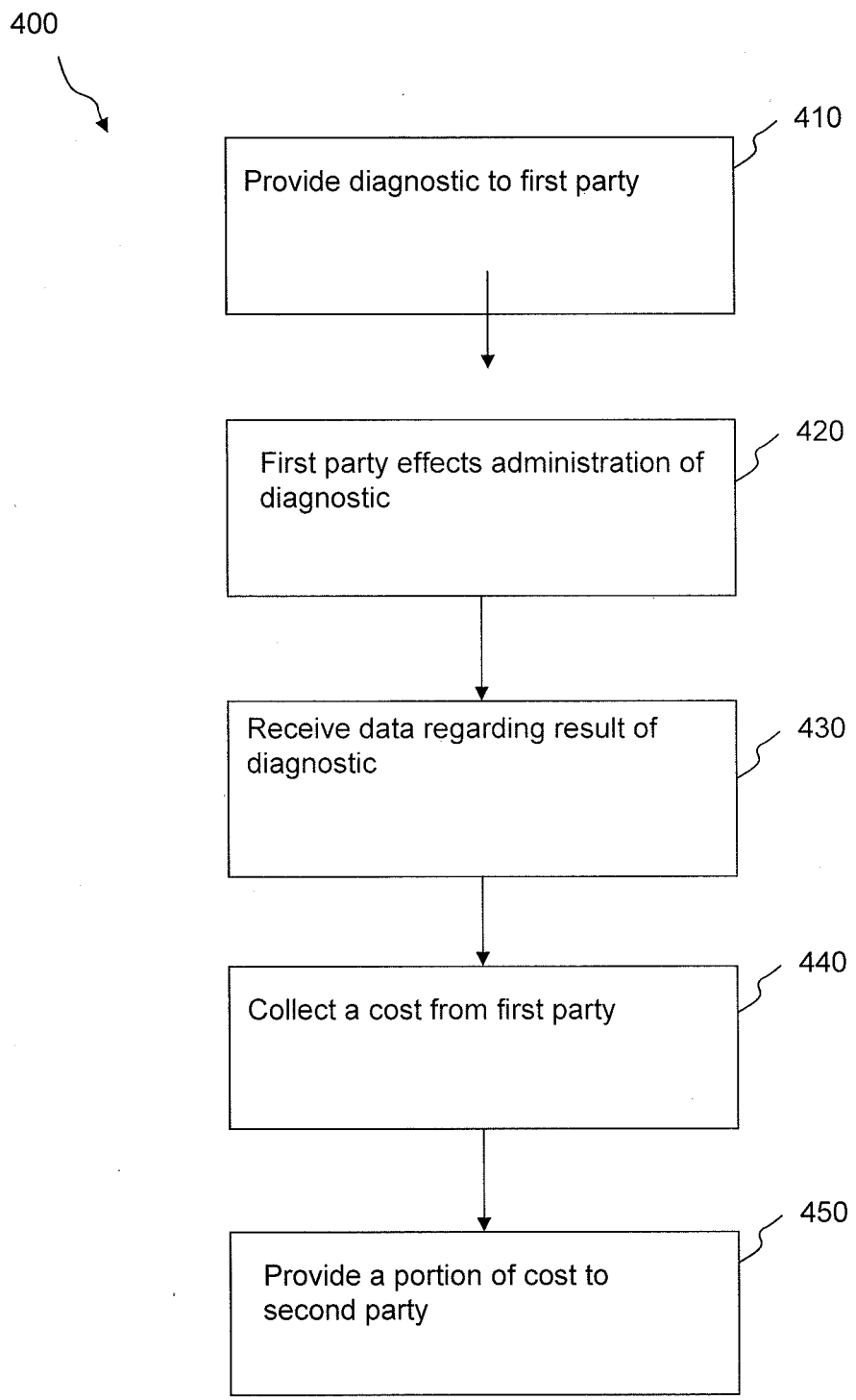
FIG. 4. is a flow chart of a process for distributing a diagnostic, according to an embodiment.

FIG. 4. is a flow chart of process 400 for distributing a diagnostic, according to an embodiment. Process 400 allows a third party to manage the distribution and cost collection of diagnostics. Process 400 can be implemented and/or realized by, for example, a clearing house or distributor of diagnostics according to the methods described herein. A diagnostic is provided to a first party at 410. The diagnostic can be provided to, for example, a hospital, a physician, an HMO, a PPO, or other entity for administering the diagnostic. In some embodiments, the diagnostic is provided directly to an individual for use.

The first party administers the diagnostic or effects administration of the diagnostic at 420. For example, an insurance company can effect administration of a diagnostic intended and approved for use without the assistance of a physician, by providing the diagnostic to an individual with instructions for use. In some embodiments, a physician administers the diagnostic to a patient.

At 430, data associated with the results of a diagnostic are received. The data can be any representation or indication of the results of a diagnostic and/or including the results of a diagnostic. As described above, the data can be, for example, a report including the results of the diagnostic, or data from the diagnostic that has not been previously analyzed to determine a result of the diagnostic. In some embodiments, the data are digital data such as, for example, a representation of a mass spectrum or assay analysis of a diagnostic. In some embodiments, the data are a blood sample, a tissue sample and/or other biological sample, for example. In some embodiments, the data can be a report such as, for example, an electronic or paper document including information associated with the diagnostic.

In some embodiments, the data are received from the first party. In other embodiments, the data are received from the person administering the diagnostic. In other embodiments, the data are received from an analyst providing some analysis of the diagnostic. For example, a diagnostic can include taking a blood sample and adding a chemical to the blood sample to test for abnormalities in blood. The blood sample with the added chemical can be analyzed by a laboratory before the data are received.

After the data are received, a cost is collected from the first party at 440. The cost collected can be based on a value of the diagnostic as described herein. In some embodiments, the cost is an additional cost that supplements an initial fee charged before the diagnostic is provided to the first party at 410, but not described in FIG. 4. In some embodiments, the cost is passed from the first party to the individual to whom the diagnostic was administered, or to an entity, such as an insurance company, responsible for some or all of the medical expenses of the individual or the first party. The cost can then be collected from the individual or other entity.

A portion of the cost is provided to a second party at 450 after the cost is collected. In some embodiments, the second party is a diagnostic manufacturer. The portion of the cost can be based on a percentage of each diagnostic price, a fixed periodic charge for the diagnostic manufacturer, and/or some other arrangement.

Process 400 can be rearranged and/or include more or fewer steps than shown in FIG. 4. For example, process 400 can include a step for calculating or determining a value of a diagnostic and/or a cost based on the value.

In some embodiments, methods and apparatus related to diagnostic pricing discussed herein can be applied to previously sequenced patient DNA. In other words, sequenced patent DNA information can be interrogated or tested by one or more diagnostics after the patient DNA information has been sequenced and stored at a memory such as a database. The DNA information in the database can be analyzed to discover and/or identify mutations, single nucleotide polymorphisms ("SNPs"), and/or markers that are related to a diagnostic or genetic test.

For example, FIG. 6 is a flow chart of process 600 for performing a diagnostic, according to an embodiment. Patient data such as DNA or other genetic material is collected, at 610, via blood, cheek or nasal swab, or other means, and that genetic material is sequenced and/or analyzed, at 620. The results of the analysis and/or sequencing can then be stored, at 630, at a memory such as a database. For example, the raw sequenced genetic data can be stored at a portion of a database at a testing facility or company. In some embodiments, that portion of the database is uniquely associated with the patient (e.g., is encrypted and/or identified by an identifier uniquely associated with the patient).

At a later time, and in some embodiments independent of the genetic material sequencing, a physician or other individual such as the patient can order a diagnostic or genetic test using the stored results of the sequencing. Patient identification data are transmitted by, for example, the physician's office to the testing company with a request for a test or diagnostic. The request for the diagnostic or test is received, at 640, and the patient identification data are matched to the sequenced DNA or genetic information (the "DNA profile") in the database at the testing company. After the patient identity is matched to the DNA profile, the test can be performed, at 650. For example, a test work order for the diagnostic or diagnostics can be queued for processing in an informatics system. An informatics system can include, for example, one or more computing devices such a computer servers configured to process DNA profiles at multiple software modules (e.g., software processes or applications) configured to implement one or more diagnostic tests to determine results of the diagnostic tests based on the DNA profiles and algorithms, patterns, and/or processes related to the diagnostic tests.

In some embodiments, the diagnostic or diagnostics are performed electronically on the DNA profile, and results are calculated for the diagnostic or diagnostics. For example, the informatics system can interrogate the DNA profile and/or other patient data for specific markers and/or sequences that are relevant to the diagnostics ordered. The informatics system can then compare the interrogated (or analyzed) portions of the DNA profile with patterns and/or algorithms that are part of the diagnostics ordered. The raw stored/banked genetic data are thereby transformed into a useful test result by the comparison to the specific markers and/or sequences that are known to have useful predictive properties. In other embodiments, the genetic data can be transformed into a useful test result using other methods and/or apparatus. In some embodiments, such patterns, algorithms, and/or related processes and apparatus are part of the intellectual property of the testing company or some other entity. The results of the diagnostic (e.g., likelihood of the presence or absence of a disease) can be determined, at 660, based on, for example, the existence or non-existence of relevant markers and/or sequences.

The results can then be stored, for example, at the database, and/or conveyed to the physician and/or patient, at 670. For example, the results of the test can be sent to a physician's office (e.g., a computing device or terminal at the physician's office) via a communications network. After the results are received, billing codes and/or patient identity information can be confirmed and payment can be processed, at 680. For example, payment can be processed as described herein.

In some embodiments, process 600 can include more or fewer steps than illustrated in FIG. 6, and/or steps can be rearranged. Similarly, some steps of process 600 can be performed by different entities. For example, a clinician or a data collection facility can collect patient data, analyze that patient data, and store that patient data. That patient data can be sent to a diagnostic facility with a request for a diagnostic test, and the diagnostic facility can use the patient data it receives from the collection facility to perform the requested diagnostic. The diagnostic facility can determine the results of the diagnostic test, send the results of the diagnostic test to the collection facility, and effect billing for the diagnostic test.

In some embodiments, one or more diagnostics (or tests) can be bundled with pre-determined pricing related to patient utility. Such a system can extract maximum value from specific panels or groups of low marginal cost tests such as genetic tests that are all—separately and/or collectively—relevant to a medical condition or disease state.

Many tests with genetic components have limited clinical utility as standalone tests. For example, results from a single test can provide useful information and identify known risk factors, but such results may not sufficiently support change of treatment decisions based on the single result or risk factors. Consider genetic variants that are known cardiac risk factors. Hundreds of clinically appropriate variants exist. Moreover, additional variants are likely to be discovered. If the test panel is not already created as a bundled package, it is often cost prohibitive for the physician to test for every variant that might show bearing on a patient's cardiac risk. A particular test, however, may be much more useful when used in conjunction with other related tests. Nevertheless, there is generally resistance to ordering a battery of all possible relevant tests due to costs. The combined value of a group of medically relevant tests run or performed at the same time, however, can be significantly greater than the sum of those same individual tests run as stand-alones. In other words, the value of the results of the combination of the tests can be of great value even when the value of each of the test individually is small.

In some embodiments, a group of tests can be combined (e.g., by a physician, a marketing company, or one or more drug manufacturers) into a single panel that is priced lower than the price of all the tests as standalones. In some embodiments, a panel can be customized to a particular patient. In other words, a panel can be patient-specific or can be a generic panel applicable to many different patients. The desired outcome is for the panel (and, thus, the diagnostics of which the panel consists) to be used more frequently than any of the tests as a stand-alone test. For example, six tests owned by six separate parties are combined in a panel that has a price of $1,000. Five of the tests are useful, but are rarely ordered as standalone, and the sixth test is more useful as a standalone, though its clinical utility (e.g., accuracy and/or precision at predicting or detecting a diseased state) is validated by the other five tests. When the test is ordered, the $1,000 is distributed to each of the first five test owners at $100 per test, and $500 is distributed to the owner of the sixth test. Thus, the rate of return to the owners of each of the tests (or to the owners of the intellectual property involved in each of the tests) as standalones can be approximated in the distribution of the cost for the panel of tests. In other words, the owner of the sixth tests receives a larger portion of the cost of the panel because the sixth test is more frequently used as a standalone than the other five tests.

Other distributions of the cost of the panel of tests to the owners of each individual test (or the owners of the intellectual property used in each of the individual tests) can also be used. For example, the owners of each individual test in the panel can receive an equal share of the cost (or profit) from the panel of tests. In some embodiments, the cost of the panel can be distributed based on a production cost of each of the individual tests. In some embodiments, the owner of the test in the panel that can validate the clinical utility of one or more other tests in the panel receives a majority share of the cost. Various other distributions of the cost of the panel of tests (or of economic benefit derived from a panel of tests by, for example, a drug manufacturer) can also be used.

In some embodiments, a multi-part pricing structure is used for groups of low-marginal cost tests (e.g. genetic tests) to maximize the validity of clinical decisions and therefore maximize the possible value to the entire group of test providers. For example, a two-part pricing structure or tariff can be utilized. A first price (e.g., zero or some other fixed price) is paid to have the panel run and analyzed. The second fixed price is paid contingent on the physician successful making an informed clinical decision based on the combined information from all test results. This second price is distributed to the owners of the individual tests or the intellectual property of the individual tests in a predetermined percentage formula. For example, a panel can include six test owned by six separate parties, and the panel that has a first price of $100 and a second price of $1,000. Five of the tests are helpful though rarely ordered as standalone, and the sixth test is more useful as a standalone and its clinical utility is validated by the other five tests. The first price can be paid immediately upon the test being ordered to cover the costs of the tests and administration thereof. The second price can be paid if, and in some embodiments only if, the clinician administering the tests or analyzing the results of the tests finds the results useful. If the results are found to be useful, the $1,000 can be distributed to each of the first five test owners at $100 per test, and $500 can be paid to the owner of the sixth test.

As discussed above, other distributions or divisions of the cost of a panel of tests (or of economic benefit derived from a panel of tests by, for example, a drug manufacturer) can also be used to compensate the owners of the individual tests in the panel. For example, the owner of each test in the panel can receive an equal share of a cost of or economic benefit derived from the panel if the results of the panel are useful to a clinician, physician, and/or patient. In some embodiments, the owners of the tests in the panel that validate the clinical utility of other tests in the panel can be compensated at a greater percentage than the owners of the tests in the panel that are validated by other tests. In other embodiments, various other distributions or divisions of the cost of a panel of tests (or of economic benefit derived from a panel of tests by, for example, a drug manufacturer) can also be used.

Additionally, in some embodiments three- or four-part (or more) pricing structures can be used. For example, one price can be paid upfront to cover the costs of a panel of tests, a second price can be paid or charged if the panel of tests suggests a first result, and a third price can be paid or charged if the panel of test suggests a second result. In some embodiments, one distribution is used to compensate the owners of the tests if the panel of tests suggests the first result and the second price is charged, and another distribution is used to compensate the owners of the tests if the panel of tests suggests the second result and the third price is charged. In some embodiments, a portion of the first cost can be distributed to one or more of the owners of the tests. For example, a portion of the first cost can be distributed to the owner of the test in the panel that is most frequently used as a standalone, and no portion of the first cost is distributed to the owners of the other tests in the panel. In other embodiments, the owner of each of the tests in the panel can receive an equal, upfront share of the first price. Various other multi-part pricing structures related to the cost of the panel of tests (or of economic benefit derived from a panel of tests by, for example, a drug manufacturer) can also be used.

FIG. 7 is a flow chart of process 700 for realizing a multipart pricing structure, according to an embodiment. A first price is charged for a diagnostic panel, at 710, and the diagnostic panel is administered, at 720. The results of the diagnostic panel are then analyzed, at 730. If the results are determined to be not useful, at 740, not additional cost or price is charged or collected, at 741. In other words, if the results of the diagnostic panel are not useful, the owners of the diagnostics in the diagnostic panel do not receive additional revenue from the diagnostic panel.

If the results of the diagnostic panel are determined to be useful, at 740, at physician or clinician can use the results of the diagnostic panel to recommend a treatment plan (e.g., a therapeutic drug regime), at 750. If results of the diagnostic panel are useful, but the physician does not recommend a treatment plan, at 750, an additional cost for the diagnostic panel is charged or collected, and is divided equally among the owners of the diagnostics in the diagnostic panel, at 751. If the physician does recommend a treatment plan, at 750, the patient can either accept or reject the treatment plan, at 760.

If the patient rejects the treatment plan, at 760, an additional cost for the diagnostic panel is charged or collected, and is divided using a first distribution among the owners of the diagnostics in the diagnostic panel, at 761. For example, the additional cost can be divided such that the owner of the diagnostic that is most frequently used as a standalone receives a disproportionate share of the additional cost and the owners of the remaining diagnostics from the diagnostic panel share equally the remainder of the additional cost. In other embodiments, other distributions can be used.

If the patient accepts the treatment plan, at 760, an additional cost for the diagnostic panel is charged or collected, and is divided using a second distribution among the owners of the diagnostics in the diagnostic panel, at 762. For example, the additional cost can be divided such that the owner of a diagnostic that validates the clinical utility of one or more of the other diagnostics in the diagnostic panel receives a disproportionate share of the additional cost and the owners of the remaining diagnostics from the diagnostic panel share equally the remainder of additional the cost. In other embodiments, other distributions can be used.

In some embodiments, process 700 can include more or fewer steps than illustrated in FIG. 7, and/or steps can be rearranged. For example, process 700 can include additional steps for determining the period of time over which the patient remains on the treatment plan and can alter the distribution of additional costs (e.g., therapeutic drug sales) that are shared among the owners of the diagnostics in the diagnostic panel over time. In other words, the percentage of an incremental value realized or effected by the diagnostic panel that each owner of the diagnostics in the diagnostic panel can vary over time (e.g., monthly or yearly) while the patient remains on the treatment plan.

In some embodiments, tests such as pharmacogenomic diagnostic tests can be used as a marketing tool for, for example, referral-fee based advertising and marketing activities for drug manufacturers. Drug manufacturers, therapeutic treatment facilities, or marketing entities on behalf of drug manufacturers or therapeutic treatment facilities, can provide low-cost or free independent tests to patients as promotional decision support materials. In other words, the tests are given away, or provided at low cost by the marketing entity at no cost to physicians and patients to indicate which patients may be best served by a specific therapeutic or therapeutic combination. Such marketing materials are similar to any other free tools, such as the Nexcura™ tool provided by the America Heart Association, that seek to aid physicians and clinicians in making correct diagnoses.

The physician or clinician administering or analyzing the results of the test is free to use or discard the information in the test results, just as he or she may discard the results of any other test in making the diagnose. The marketing company can be paid a per-referral fee by the sponsoring company (e.g., drug manufacturer or therapeutic treatment facility) for each patient prescribed the drug or therapy or that is identified as a good candidate for the therapy by a physician or clinician. In some embodiments, the marketing company is paid the per-referral fee if the patient agrees to and begins the therapy. The physician is paid a reimbursement for the blood draw in an amount commensurate the normal reimbursement for the test, if it were a regular paid test. Thus, the doctor's independent judgment regarding patient care is uncompromised because the marketing company does not act on behalf of a physician in selecting the particular therapy, and the physician is not compensated for prescribing a particular therapy or course of treatment. Moreover, neither the physician nor the patient is obligated to select a particular course of treatment if the test (or a panel of tests) provides a predetermined result. In other words, the purchase of a particular therapy is not tied to the receiving of the free or low cost test. Furthermore, the physician is not compensated for enrolling his patients into the promotional testing program. Rather, the physician and patient are provided with low-cost tools to select a favorable course of treatment, and the financial beneficiary of that course of treatment (e.g., drug company or therapeutic treatment facility) receives increased distribution of information about its services and/or products to patients who will most benefit from those services and/or products.

For example, a marketing company can provide full reimbursement for diagnostic tests for statin therapeutic response. A physician can use the information from a diagnostic test or a panel of diagnostic tests to help decide on a course of treatment that may or may not include a particular statin therapy. Such a marketing initiative requires a computer system for tracking patient outcomes for those patients who receive the free test to calculate effectiveness yield of the marketing campaign and determine reimbursement over time. The arms-length relationships between the marketing company providing (e.g., giving away) the tests, the physician, and therapeutic company prevents potential conflicts of interest.

In some embodiments, a third party tracks and/or manages calculated values of diagnostics, payments to and from various parties for diagnostics, and/or contractual conditions agreed upon at the time of the diagnostic. For example, an individual might agree to purchase a therapeutic treatment for a predetermined amount of time if the diagnostic produces a particular result, in exchange for receiving the diagnostic at a reduced cost. In some embodiments, the third party can track, record, calculate, audit and/or adjust recurring payments resulting from the use of the diagnostic. For example, if a person was prescribed a therapeutic drug as a result of a diagnostic and stayed on a therapeutic treatment for 10 years, the third party can collect from a payor a diagnostic fee each year until the patient stops taking the drug.

In some embodiments, if the patient discontinues the therapeutic treatment, payments also cease. In other embodiments, payments for the diagnostic continue for a fixed period of time regardless of continued use of a therapeutic treatment. In some embodiments, payments for the diagnostic can end before the therapeutic treatment ends. For example, if the patient stayed on a therapeutic treatment for 30 years, the third party may collect payments for only 20 years.

In some embodiments, individual patients have their diagnostic and therapeutic treatment usage tracked and recorded by the third party and future liabilities estimated by the third party, connected parities, or unassociated parties through predictive and actuarial analysis.

In one embodiment, the third party manages payments from insurance companies when individuals who have received the diagnostic change insurance companies or insurance plans. For example, the third party can stop collecting from the insurance company of a patient who switches providers, and begin charging the new insurance provider, if any, for the continuing diagnostic costs of the patient. Additionally, the third party can collect from an individual any costs not covered by the individual's insurance coverage.

In one embodiment, a computing device including, for example, a processor and a memory is used to calculate, manage and/or track transactions, and net them to each party (e.g., diagnostic manufacturer, insurance company, drug manufacture) based on each party's net inflow and/or outflow of diagnostic payments.

Figure 5:
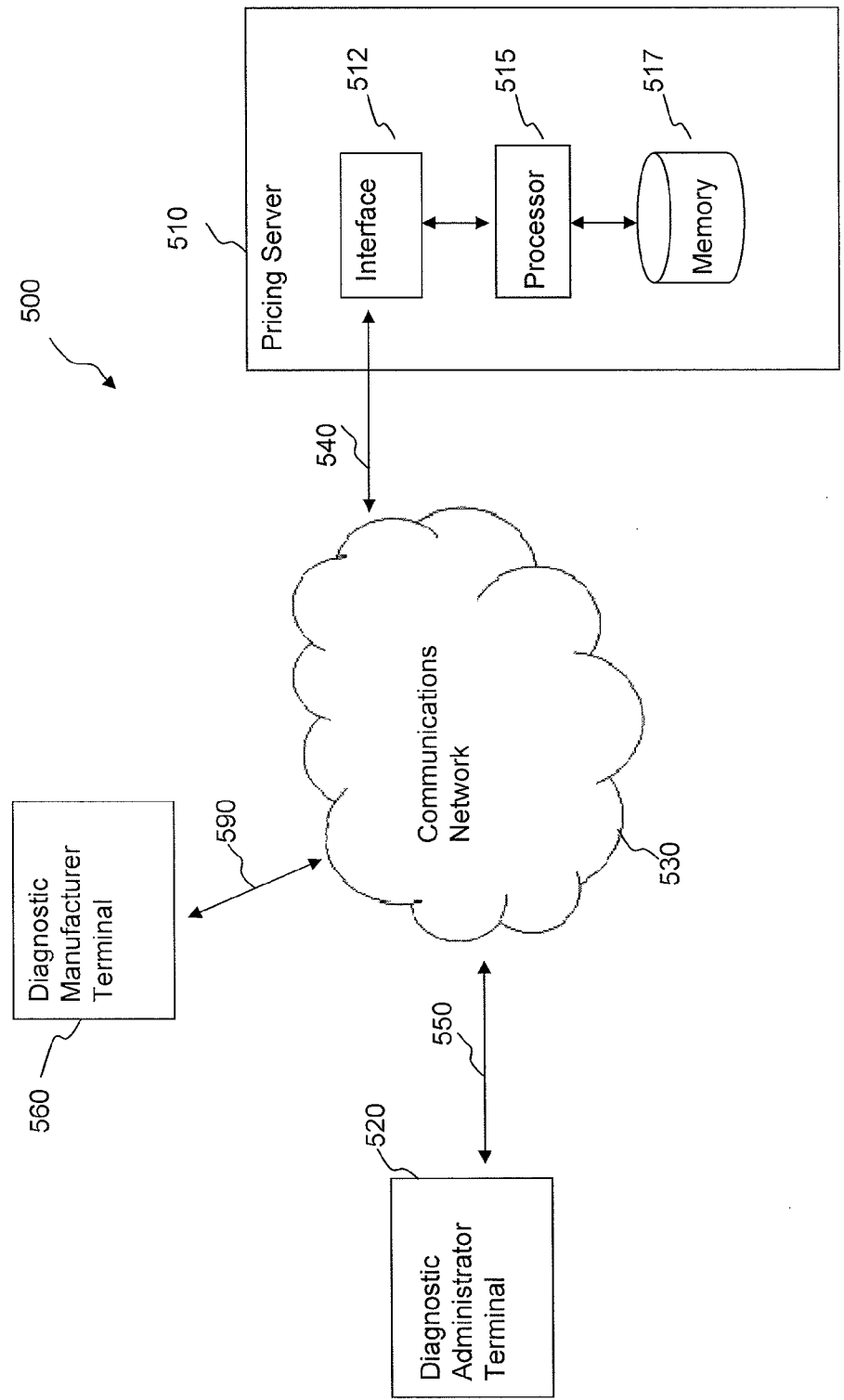
FIG. 5 is a system block diagram of a system for pricing a diagnostic, according to an embodiment.

FIG. 5 is a system block diagram of system 500 for pricing a diagnostic, according to an embodiment. System 500 includes pricing server 510, diagnostic manufacturer terminal 560 and diagnostic administrator terminal 520 operatively coupled to communications network 530. Communications network can be, for example, a computer network or a telephony network. In some embodiments, communications network can be a combination of networks coupled one to another by, for example, network bridges, routers, switches and/or gateways.

Pricing server 510 can be associated with any entity managing, tracking and/or administering diagnostics pricing. For example, a clearing house for managing diagnostics pricing between one or more diagnostic manufacturers and one or more diagnostics administrators such as insurance companies, drug manufacturers and hospitals can be associated with a pricing server. In some embodiments, pricing server 510 can be directly associated with a diagnostics manufacturer.

Diagnostic manufacturer terminal 560 can be associated with a manufacturer of diagnostics and/or a diagnostics distributor. Diagnostic administrator terminal 520 can be associated with any entity responsible for and/or directly or indirectly effecting administration of diagnostics. For example, a diagnostics administrator such as an insurance company, a drug manufacturer or a hospital.

Pricing server 510 is coupled to communications network 530 via connection 540; diagnostic manufacturer terminal 560 is coupled to communications network 530 via connection 590; and diagnostic administrator terminal 520 is coupled to communications network 530 via connection 550. Connections 540, 550 and 590 are any connections suitable for coupling pricing server 510, diagnostic manufacturer terminal 560 and diagnostic administrator terminal 520 to communications network 530.

As illustrated in FIG. 5, pricing server 510 includes interface 512, processor 515 and memory 517. Processor 515 is operatively coupled to interface 512 and memory 517. Diagnostic manufacturer terminal 560 and diagnostic administrator terminal 520 include similar elements to processor 515, interface 512 and memory 517 of pricing server 510.

Processor 515 can be any of a variety of processors. Such processors can be implemented, for example, as hardware modules such as embedded microprocessors, microprocessors as part of a computer system, Application-Specific Integrated Circuits ("ASICs"), and Programmable Logic Devices ("PLDs"). Some such processors can have multiple instruction executing units or cores. Such processors can also be implemented as one or more software modules in programming languages as Java™, C++, C, assembly, a hardware description language, or any other suitable programming language. A processor according to some embodiments includes media and computer code (also can be referred to as code) specially designed and constructed for the specific purpose or purposes.

Interface 512 can be any interface configurable to be operatively coupled to communication network 530 via connection 540. For example, a network interface can be a wireless interface such as, for example, a worldwide interoperability for microwave access ("WiMAX") interface, a high-speed packet access ("HSPA") interface, and/or a WLAN interface. A network interface can also be, for example, an Ethernet interface, a broadband interface, a fiber-optic interface, and/or a telephony interface.

Memory 517 can be a read-only memory ("ROM"); a random-access memory ("RAM") such as, for example, a magnetic disk drive, and/or solid-state RAM such as static RAM ("SRAM") or dynamic RAM ("DRAM"); and/or FLASH memory or a solid-data disk ("SSD"). In some embodiments, a memory can be a combination of memories. For example, a memory can include a DRAM cache coupled to a magnetic disk drive and an SSD.

In addition to memory 517, some embodiments include another processor-readable medium (not shown in FIG. 5) having instructions or computer code thereon for performing various processor-implemented operations. Examples of processor-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks; solid-state memory such as SSDs and FLASH memory; and ROM and RAM devices. Examples of computer code include, but are not limited to, micro-code or micro-instructions, machine instructions (such as produced by a compiler), and files containing higher-level instructions that are executed by a computer using an interpreter. For example, an embodiment may be implemented using Java™, C++, or other object-oriented programming language and development tools. Additional examples of computer code include, but are not limited to, control signals, encrypted code, and compressed code.

Pricing server 510 can send and receive data associated with diagnostics from diagnostic administrator terminal 520, diagnostic manufacturer 560, and/or other terminals not shown in FIG. 5 via communications network 530. For example, pricing server 510 can send and receive data associated with the results of a diagnostic, diagnostic pricing data and/or financial data.

Additionally, pricing server 510 can determine and/or calculate, for example, the value of a diagnostic, a price of a diagnostic and/or other information relating to a diagnostic according to embodiments described herein. For example, pricing server 510 can be operated by a clearing house for managing payments and/or for distribution of diagnostics.

In some embodiments, system 500 can include more or fewer terminals and/or servers. For example, multiple diagnostic manufacturer terminals and/or diagnostic administrator terminals can be operatively coupled to a single pricing server via a communications network. Additionally, a pricing server can operate independent of diagnostic manufacturer terminals and/or diagnostic administrator terminals and a communications network. For example, a diagnostic manufacturer can use a pricing server internally to automatically determine values and prices associated with one or more diagnostics.

In one embodiment, a marketplace is created where future diagnostic healthcare liabilities are combined and securitized into groups of liabilities, or "tranches." For example, as a result of a pricing embodiment whereby a third party can begin charging a new insurance provider for future diagnostic value generated for a past diagnostic if a patient switches insurance providers, the insurance company may wish to make certain all future costs associated with such liabilities. Such insurance companies could bundle their liabilities and "sell" such liabilities to another party, thereby locking in gains from their diagnostic use and purchase strategy and eliminating future payment exposure. In another embodiment, such liabilities tranches could also be expanded to comprise the future medical liabilities of any individuals, or groups of individuals, not limited to just diagnostic liabilities. For example, insurance plans may one day require that contingent liabilities for pre-existing conditions to be paid for by a prior insurer. In such a case, these liabilities on future medical cost exposure could also be bundled and securitized to enable the transfer of risk for these liabilities.

In one embodiment, a method of pricing a diagnostic test administered to a test subject includes receiving data associated with the diagnostic test and including an indication of one of a first result of the diagnostic test and a second result of the diagnostic test, and setting a price of the diagnostic test based on the indication. In some embodiments, setting a price of the diagnostic tests includes setting the price based at least in part on a recurring cost of a therapeutic treatment associated with the indication. In some embodiments, the method also includes charging a recurring payment for the diagnostic test based on the price of the diagnostic test. In some embodiments, the method also includes determining a value associated with the indication.

In some embodiments, the first result indicates the presence of a disease and the second result indicates the absence of the disease. In some embodiments, the first result indicates that a therapeutic treatment is desirable and the second result indicates that the therapeutic treatment is not desirable. In some embodiments, the first result indicates that a therapeutic treatment is desirable and the second result indicates that the therapeutic treatment is not desirable.

In some embodiments, the price is greater if the indication is of the first result that the price if the indication is of the second result. In one embodiment, the price is at least one hundred times greater if the indication is of the first result than the price if the indication is of the second result. In some embodiments, the price is zero if the indication is of the second result. In some embodiments, the price is variable over time and based on the outcome of a therapeutic treatment.

In one embodiments, a method of pricing a diagnostic test includes receiving data associated with the diagnostic test and including an indication of one of a first result of the diagnostic test and a second result of the diagnostic test, charging a first price for the diagnostic test if the indication is of the first result, and charging a second price greater than the first price for the diagnostic test if the indication is of the second result. In some embodiments, the first price and/or the second price are predetermined (i.e., are determined before the data are received). In some embodiments, a portion of one of the first price and the second price is refunded if the indication is incorrect, inaccurate or erroneous.

In some embodiments, the first result occurs at least twice as often as the second result in a general population. For example, a result indicating that an individual has a rare disease occurs no more than once for every twenty individuals screened for the disease in a country.

In some embodiments, the first price is charged to a first party if the indication is of the first result, and the second price is charged to a second party if the indication is of the second result. The second party is different from the first party.

In some embodiments, the second price is a recurring payment. For example, a charge or payment made monthly. In some embodiments, the second price is based on a cost of a therapeutic treatment. In some embodiments, the therapeutic treatment is associated with the second result. For example, the second result can indicate that the therapeutic treatment will likely be effective in a particular patient.

In one embodiment, a method of determining a price for a diagnostic test includes, receiving data associated with the diagnostic test and including an indication of one of a first result of the diagnostic test and a second result of the diagnostic test, calculating a value of the diagnostic test based on the indication, and determining the price for the diagnostic test based on the value. In some embodiments, the indication is of the first result, the first result indicates a desirability of a therapeutic treatment having a treatment period, and the price is based on the value of the diagnostic test over the treatment period.

In some embodiments, the first result indicates a disease state and the second result indicates a non-disease state. In some embodiments, the first result indicates a predicted disease state and the second result indicates a predicted non-disease state. In some embodiments, the first result indicates that a therapeutic treatment is desirable and the second result indicates that the therapeutic treatment is not desirable.

In one embodiment, a method of pricing a diagnostic test includes charging a first price for the diagnostic test before the diagnostic test is administered, receiving data associated with the diagnostic test and including an indication of one of a first result of the diagnostic test and a second result of the diagnostic test, charging a second price for the diagnostic test if the indication is of the first result and a third price for the diagnostic test if the indication is of the second result. In some embodiments, the second price is a recurring payment and the third price is a one-time payment. In some embodiments, the second price is associated with a cost of a therapeutic treatment. In some embodiments, the second price is associated with a recurring cost of a therapeutic treatment. In some embodiments, one of the second price and the third price is zero.

In some embodiments, the first result indicates a disease state and the second result indicates a non-disease state. In some embodiments, the first result indicates that a therapeutic treatment is desirable and the second result indicates that the therapeutic treatment is not desirable. In some embodiments, the method also includes selecting a therapeutic treatment based on the indication if the indication is of the second result, and delaying the charging of the second price until the therapeutic treatment has provided a useful result.

In one embodiment, a method of distributing a diagnostic test includes providing the diagnostic test to a first party, collecting a first cost based on the result of the diagnostic test, and providing a portion of the first cost to a second party. In some embodiments, the first party effects administration of the diagnostic test to an individual. In some embodiments, the first cost is collected from the first party. In some embodiments, the first cost is collected from a party other than the first party.

In some embodiments, a second cost is collected from a party other than the first party, and a portion of the second cost is provided to the second party. In some embodiments, the diagnostic test is received from the second party at a second cost before the diagnostic test is provided to the first party. In some embodiments, the second cost is determined based on an economic value of a possible or expected result of the diagnostic test.

While certain embodiments have been shown and described above, various changes in form and details may be made. For example, some features of embodiments that have been described in relation to a particular embodiment or process can be useful in other embodiments. Some embodiments that have been described as methods can be implemented as software or as digital or analog hardware. Additionally, although methods and apparatus described herein have been described with reference to medical diagnostics, the methods of pricing described herein can be applied to pharmaceutical drugs, or other medical services and/or devices. Particularly when an outcome or result of such pharmaceutical drugs and medical services and/or devices can be measured or determined. For example, a drug or medical device is prescribed and given for a low/minimal initial price, and upon successful remedy of the condition or disease being treated, a higher or additional price is triggered or charged. Furthermore, although methods and apparatus described herein have been described with reference to manufacturers, these methods and apparatus can be equally applicable to distributors and/or other entities other than manufactures that provide medical diagnostics.

It should be understood that the systems and methods described herein can include various combinations and/or sub-combinations of the components and/or features of the different embodiments described. For example, steps and aspects of one process described herein can be combined with steps and aspects of one or more other processes described here. Thus, features described with reference to one or more embodiments can be combined with other embodiments described herein.

What is claimed is:

1. A method of pricing a single diagnostic test administered to a test subject, comprising:
   receiving at a computer data associated with the single diagnostic test, the data including an indication of one of a first result of the single diagnostic test and a second result of the single diagnostic test; and
   setting by a processor of the computer a price for the single diagnostic test to a first price, when the indication is of the first result of the single diagnostic test, and setting the price for the single diagnostic test to a second price, when the indication is of the second result of the single diagnostic test, the second price being different from the first price.

2. The method of claim 1, further comprising charging a recurring payment for the single diagnostic test based on the set price.

3. The method of claim 1, wherein the first price is greater than the second price.

4. The method of claim 1, wherein the first price is at least one hundred times greater than the second price.

5. The method of claim 1, further comprising determining by the processor a value associated with the indication.

6. The method of claim 1, wherein the first result indicates the presence of a disease and the second result indicates the absence of the disease.

7. The method of claim 1, wherein the first result indicates that a therapeutic treatment is desirable and the second result indicates that the therapeutic treatment is not desirable.

8. The method of claim 1, wherein the setting by the processor includes setting the price based at least in part on a recurring cost of a therapeutic treatment associated with the indication.

9. The method of claim 1, wherein the set price is zero if the indication is of the second result.

10. The method of claim 1, wherein the set price is variable over time and based on the outcome of a therapeutic treatment.

11. The method of claim 1, wherein:
    the setting by the processor the price of the single diagnostic includes the processor accessing a data set at a database, the data set associated with one of the first result of the single diagnostic test and the second result of the single diagnostic test.

12. A method of pricing a single diagnostic test, comprising:
    receiving at a computing device data associated with the single diagnostic test, the data including an indication of one of a first result of the single diagnostic test and a second result of the single diagnostic test;

charging a first price for the single diagnostic test upon the received indication being of the first result; and charging a second price greater than the first price for the single diagnostic test upon the received indication being of the second result.

13. The method of claim 12, wherein the second price is structured as a recurring payment.

14. The method of claim 12, wherein the second price is based on a cost of a therapeutic treatment, the therapeutic treatment being associated with the second result.

15. The method of claim 12, wherein the first result occurs at least twice as often as the second result in a general population.

16. The method of claim 12, wherein:
the first price is charged to a first party if the indication is of the first result; and
the second price is charged to a second party different from the first party if the indication is of the second result.

17. The method of claim 12, further comprising:
determining by the computer the first price based on a first presumed result for the single diagnostic test before the receiving; and
determining by the computer the second price based on a second presumed result for the single diagnostic test before the receiving.

18. The method of claim 12, further comprising refunding a portion of one of the first price and the second price if the indication is incorrect.

19. The method of claim 12, wherein the computing device is a first computing device, and wherein the data are received from a second computing device associated with an administrator of a diagnostic via a communications network, the method further comprising:
sending from the first computing device the first price and the second price to a third computing device associated with a diagnostic manufacturer via the communications network.

20. A method of determining a price for a single diagnostic test, comprising:
receiving at a computing device data associated with the single diagnostic test, the data including an indication of one of a first result of the single diagnostic test and a second result of the single diagnostic test;
calculating on a processor of the computing device a value for the single diagnostic test to be a first value, when the indication is of the first result of the single diagnostic test, and to be a second value, when the indication is of the second result of the single diagnostic test, the second value being different from the first value; and
determining on the computing device the price for the single diagnostic test based on the calculated value.

21. The method of claim 20, wherein the first result indicates a disease state and the second result indicates a non-disease state.

22. The method of claim 20, wherein the first result indicates a predicted disease state and the second result indicates a predicted non-disease state.

23. The method of claim 20, wherein the first result indicates that a therapeutic treatment is desirable and the second result indicates that the therapeutic treatment is not desirable.

24. The method of claim 20, wherein:
the indication is of the first result;
the first result indicates a desirability of a therapeutic treatment, the therapeutic treatment having a treatment period; and
the price is based on the calculated value over the treatment period.

25. The method of claim 20, wherein the computing device is a first computing device and wherein the calculating on the first computing device includes accessing a value associated with one of the first result of the single diagnostic test and the second result of the single diagnostic test at a database, the method further comprising:
sending the price to a second computing device associated with a diagnostic administrator via a communications network.

26. A method of pricing a single diagnostic test, comprising:
charging a first price for the single diagnostic test before administration of the single diagnostic test;
receiving at a computing device data associated with the single diagnostic test, the data including an indication of one of a first result of the single diagnostic test and a second result of the single diagnostic test; and
charging a second price for the single diagnostic test if upon the received indication being of the first result and a third price for the single diagnostic test upon the received indication being of the second result, the first price, second price and third price being different from each other.

27. The method of claim 26, wherein the second price is a recurring payment and the third price is a one-time payment.

28. The method of claim 26, wherein the first result indicates a disease state and the second result indicates a non-disease state.

29. The method of claim 26, wherein the first result indicates that a therapeutic treatment is desirable and the second result indicates that the therapeutic treatment is not desirable.

30. The method of claim 26, wherein the second price is associated with a recurring cost of a therapeutic treatment.

31. The method of claim 26, wherein the second price is associated with a cost of a therapeutic treatment.

32. The method of claim 26, wherein the second price is zero.

33. The method of claim 26, further comprising:
selecting a therapeutic treatment based on the indication if the indication is of the second result; and
delaying the charging of the second price until the therapeutic treatment has provided a useful result.

34. The method of claim 26, wherein the computing device is a first computing device, and further comprising:
sending by the first computing device via a communications network, before the receiving, a patient identifier to a second computing device configured to process a diagnostic based on an existing DNA profile of a patient associated with the patient identifier, the DNA profile stored at a database operatively coupled to the second computing device, the data being received at the first computing device from the second computing device via the communications network.

35. A method of distributing a single diagnostic test, comprising:
providing the single diagnostic test to a first party, the first party effecting administration of the single diagnostic test to an individual;
receiving at a computing device data associated with a result of the single diagnostic test, the data including an indication of one of a first result of the single diagnostic test and a second result of the single diagnostic test;
collecting a first cost based on one of a first economic value of the result of the single diagnostic test, when the indication is of the first result of the single diagnostic test, and a second economic value of the result of the single diagnostic test, when the indication is of the second result of the single diagnostic test, the second economic value being different from the first economic value; and providing a portion of the first cost to a second party.

36. The method of claim 35, wherein the collecting is from the first party.

37. The method of claim 35, wherein the collecting is from a party other than the first party.

38. The method of claim 35, further comprising:
collecting a second cost from a party other than the first party; and
providing a portion of the second cost to the second party.

39. The method of claim 38, further comprising determining by a processor of the computing device the second cost based on one of the first economic value of the result of the single diagnostic test and the second economic value of the result of the single diagnostic test.

40. The method of claim 35, further comprising receiving the diagnostic test from the second party at a second cost before the providing the diagnostic test to the first party.

41. The method of claim 35, wherein the data are received via a communications network at the computing device having a processor programmed configured to determine the first cost, the method further comprising:
sending from the computing device to the first party via the communications network the first cost.

42. The method of claim 35, wherein the diagnostic test is a panel of diagnostic tests and the portion of the first cost is a first portion of the first cost, the method further comprising:
providing a second portion of the first cost to a third party, the second portion of the first cost different from the first portion of the first cost.

43. A method, comprising:
storing a data set associated with a DNA profile at a memory of a computer at a first time;
receiving a request for a diagnostic of the data set at a second time after the first time;
producing on a processor of the computer a result based on an analysis of the data set, the analysis based on the requested diagnostic, the result being one of a first result indicating the existence of a genetic marker and a second result indicating the absence of a genetic marker;
defining on the processor of the computer a first price associated with the result of the requested diagnostic upon the result being the first result; and
defining on the processor of the computer a second price different from the first price, associated with the requested diagnostic upon the result being the second result.

44. The method of claim 43, wherein:
the first result is associated with a diseased state; and
the second result is associated with a non-diseased state.

45. A method comprising:
providing a single diagnostic panel to a first party, the first party effecting administration of the single diagnostic panel to an individual, the single diagnostic panel including a first diagnostic test and a second diagnostic test;
receiving at a processor of a computing device data associated with a result of the diagnostic panel, the data including an indication of one of a first result of the single diagnostic panel and a second result of the single diagnostic panel;
collecting a cost based on one of a first economic value of the result of the single diagnostic panel, when the indication is of the first result of the single diagnostic panel, and a second economic value of the result of the single diagnostic test, when the indication is of the second result of the single diagnostic test, the second economic value being different from the first economic value;
providing a first portion of the cost to a second party, the second party associated with the first diagnostic test; and
providing a second portion of the cost to a third party, the first portion being greater than the second portion, the third party associated with the second diagnostic test.

46. The method of claim 45, wherein the cost is a first cost, the method further comprising:
collecting, before the receiving, a second cost.

47. The method of claim 45, wherein the computing device is a first computing device, and wherein the data are received from a second computing device associated with a diagnostic administrator via a communications network.

* * * * *

UNITED STATES PATENT AND TRADEMARK OFFICE
CERTIFICATE OF CORRECTION

PATENT NO. : 8,706,528 B2
APPLICATION NO. : 12/499505
DATED : April 22, 2014
INVENTOR(S) : Johnson It is certified that error appears in the above-identified patent and that said Letters Patent is hereby corrected as shown below:

In the Claims

Claim 26, column 26, line 18:

after "test" delete "if"

Claim 41, column 27, line 22:

after "programmed" delete "configured"

Signed and Sealed this
Twenty-third Day of December, 2014

Michelle K. Lee
*Deputy Director of the United States Patent and Trademark Office*